(12) United States Patent
Loebl et al.

(10) Patent No.: US 10,149,770 B2
(45) Date of Patent: *Dec. 11, 2018

(54) ORTHOPEDIC IMPLANT WITH ADJUSTABLE ANGLE BETWEEN TISSUE CONTACT SURFACES

(71) Applicant: SEASPINE, INC., Carlsbad, CA (US)

(72) Inventors: Oded Loebl, Tel Mond (IL); Didier Toubia, Raanana (IL); Haim Yustein, Netanya (IL)

(73) Assignee: SEASPINE, INC., Carlsbad, CA (US)

( * ) Notice: Subject to any disclaimer, the term of this patent is extended or adjusted under 35 U.S.C. 154(b) by 405 days.

This patent is subject to a terminal disclaimer.

(21) Appl. No.: 14/165,614

(22) Filed: Jan. 28, 2014

(65) Prior Publication Data
US 2015/0018951 A1      Jan. 15, 2015

Related U.S. Application Data

(60) Provisional application No. 61/843,957, filed on Jul. 9, 2013, provisional application No. 61/897,898, filed on Oct. 31, 2013.

(51) Int. Cl.
*A61F 2/44* (2006.01)
*A61F 2/46* (2006.01)
*A61F 2/30* (2006.01)

(52) U.S. Cl.
CPC .............. *A61F 2/4425* (2013.01); *A61F 2/44* (2013.01); *A61F 2/442* (2013.01); *A61F 2/447* (2013.01);
(Continued)

(58) Field of Classification Search
CPC .. A61F 2002/30471; A61F 2002/30373; A61F 2002/30522; A61F 2002/30538; A61F 2/44; A61F 2/447
(Continued)

(56) References Cited

U.S. PATENT DOCUMENTS

| 4,759,769 A | 7/1988 | Hedman et al. |
| 5,059,193 A | 10/1991 | Kuslich |

(Continued)

FOREIGN PATENT DOCUMENTS

| DE | 2263842 | 7/1974 |
| DE | 9107494 | 9/1991 |

(Continued)

OTHER PUBLICATIONS

E. AliCl, et al "Prostheses Designed for Vertebral Body Replacement" in Journal of Biomechanics vol. 23 1990, No. 8. pp. 799-809.

*Primary Examiner* — Zade Coley
*Assistant Examiner* — Jessica Weiss
(74) *Attorney, Agent, or Firm* — Middleton Reutlinger; Robert H. Eichenberger; Chad D. Bruggeman

(57) ABSTRACT

An implant having a base with a first contact surface and a hinged element, hingedly interconnected with a first portion of the base, providing a second contact surface. The first portion of the base is displaceable relative to a second portion so that the base can be shortened from an initial length towards a second length. A linking segment is hingedly connected to both the second portion of the base and to the hinged element so that shortening of the base causes the linking segment to push a region of the hinged element away from the base, thereby changing an angle of the second contact surface relative to the first contact surface.

28 Claims, 19 Drawing Sheets

(52) U.S. Cl.
CPC .......... *A61F 2/4455* (2013.01); *A61F 2/4611* (2013.01); *A61F 2002/3055* (2013.01); *A61F 2002/30373* (2013.01); *A61F 2002/30471* (2013.01); *A61F 2002/30522* (2013.01); *A61F 2002/30538* (2013.01); *A61F 2002/30904* (2013.01); *A61F 2002/4623* (2013.01); *A61F 2002/4627* (2013.01); *A61F 2002/4629* (2013.01); *A61F 2310/00023* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 5,171,278 | A | 12/1992 | Pisharodi |
| 5,258,031 | A | 11/1993 | Salib et al. |
| 5,390,683 | A | 2/1995 | Pisharodi |
| 5,534,029 | A | 7/1996 | Shima |
| 5,599,279 | A | 2/1997 | Slotman |
| 5,620,458 | A | 4/1997 | Green et al. |
| 6,039,761 | A | 3/2000 | Li et al. |
| 6,080,193 | A | 6/2000 | Hochshuler et al. |
| 6,126,689 | A * | 10/2000 | Brett ................ A61F 2/4455 623/17.15 |
| 6,190,414 | B1 | 2/2001 | Young et al. |
| 6,193,757 | B1 | 2/2001 | Foley |
| 6,238,403 | B1 | 5/2001 | Greene, Jr. et al. |
| 6,332,894 | B1 | 12/2001 | Stalcup et al. |
| 6,368,351 | B1 | 4/2002 | Glenn |
| 6,375,682 | B1 | 4/2002 | Fleischmann et al. |
| 6,387,130 | B1 | 5/2002 | Stone et al. |
| 6,419,705 | B1 | 7/2002 | Erickson |
| 6,443,989 | B1 | 9/2002 | Jackson |
| 6,491,724 | B1 * | 12/2002 | Ferree ................ A61F 2/30742 623/17.11 |
| 6,576,016 | B1 | 6/2003 | Hochshuler et al. |
| 6,582,451 | B1 | 6/2003 | Marucci et al. |
| 6,620,196 | B1 | 9/2003 | Trieu |
| 6,641,614 | B1 | 11/2003 | Wagner et al. |
| 6,676,665 | B2 | 1/2004 | Foley et al. |
| 6,706,070 | B1 | 3/2004 | Wagner et al. |
| 6,830,589 | B2 | 12/2004 | Erickson |
| 7,070,598 | B2 | 7/2006 | Lim et al. |
| 7,087,055 | B2 | 8/2006 | Lim et al. |
| 7,097,648 | B1 | 8/2006 | Globerman et al. |
| 7,938,860 | B2 | 7/2008 | Amano |
| 7,431,735 | B2 | 10/2008 | Liu et al. |
| 7,621,956 | B2 | 11/2009 | Paul |
| 7,625,377 | B2 | 12/2009 | Veldhuizen et al. |
| 7,641,690 | B2 | 1/2010 | Abdoiu |
| 7,655,046 | B2 | 2/2010 | Dryer et al. |
| 7,720,282 | B2 | 5/2010 | Blake et al. |
| 7,763,028 | B2 | 7/2010 | Lim et al. |
| 7,799,081 | B2 | 9/2010 | McKinley |
| 7,846,206 | B2 | 12/2010 | Oglaza et al. |
| 7,850,734 | B2 | 12/2010 | Oh |
| 7,901,409 | B2 | 3/2011 | Canaveral et al. |
| 7,905,920 | B2 | 3/2011 | Galea |
| 7,909,872 | B2 | 3/2011 | Zlpnick et al. |
| 7,947,078 | B2 | 5/2011 | Siegal |
| 7,959,652 | B2 | 6/2011 | Zucherman et al. |
| 8,021,429 | B2 | 9/2011 | Viker |
| 8,025,665 | B2 | 9/2011 | Lim et al. |
| 8,062,375 | B2 | 11/2011 | Glerum et al. |
| 8,123,809 | B2 | 2/2012 | Melkent et al. |
| 8,133,232 | B2 | 3/2012 | Levy et al. |
| 8,187,332 | B2 | 3/2012 | Moluen et al. |
| 8,292,963 | B2 | 10/2012 | Miller et al. |
| 8,303,658 | B2 | 11/2012 | Peterman |
| 8,308,802 | B2 | 11/2012 | Rhoda et al. |
| 8,317,798 | B2 | 11/2012 | Lim et al. |
| 8,317,802 | B1 | 11/2012 | Manzi et al. |
| 8,317,866 | B2 | 11/2012 | Palmatier et al. |
| 8,323,344 | B2 | 12/2012 | Galeey et al. |
| 8,337,531 | B2 | 12/2012 | Johnson et al. |
| 8,337,559 | B2 | 12/2012 | Hanseel et al. |
| 8,343,193 | B2 | 1/2013 | Johnson et al. |
| 8,349,013 | B2 | 1/2013 | Zucherman et al. |
| 8,349,014 | B2 | 1/2013 | Barreiro et al. |
| 8,377,071 | B2 | 2/2013 | Lim et al. |
| 8,398,713 | B2 | 3/2013 | Weiman |
| 8,403,990 | B2 | 3/2013 | Dryer et al. |
| 8,444,697 | B1 | 5/2013 | Butler et al. |
| 8,518,120 | B2 | 8/2013 | Glerum et al. |
| 8,523,944 | B2 | 9/2013 | Jimenez et al. |
| 8,556,979 | B2 | 10/2013 | Glerum et al. |
| 8,579,907 | B2 | 11/2013 | Lim et al. |
| 8,628,576 | B2 | 1/2014 | Triplett et al. |
| 8,628,577 | B1 * | 1/2014 | Jimenez ................ 623/17.15 |
| 8,679,183 | B2 | 3/2014 | Glerum et al. |
| 8,685,098 | B2 | 4/2014 | Glerum et al. |
| 8,709,086 | B2 | 4/2014 | Glerum |
| 8,771,360 | B2 | 7/2014 | Jimenez et al. |
| 8,870,959 | B2 | 10/2014 | Arnin |
| 9,005,291 | B2 * | 4/2015 | Loebl ................ A61F 2/4425 623/17.15 |
| 9,017,413 | B2 | 4/2015 | Siegal |
| 2002/0015197 | A1 | 2/2002 | Foley et al. |
| 2002/0151976 | A1 * | 10/2002 | Foley ................ A61F 2/4455 623/17.11 |
| 2003/0236520 | A1 | 12/2003 | Lim et al. |
| 2004/0059418 | A1 | 3/2004 | Mckay et al. |
| 2004/0133280 | A1 | 7/2004 | Trieu |
| 2004/0162618 | A1 | 8/2004 | Mujwid et al. |
| 2004/0193158 | A1 | 9/2004 | Lim et al. |
| 2005/0033431 | A1 | 2/2005 | Gordon et al. |
| 2005/0060036 | A1 | 3/2005 | Schultz |
| 2005/0113920 | A1 | 5/2005 | Foley et al. |
| 2005/0125062 | A1 | 6/2005 | Biedermann et al. |
| 2005/0143827 | A1 | 6/2005 | Globerman et al. |
| 2005/0182416 | A1 | 8/2005 | Lim et al. |
| 2005/0209698 | A1 | 9/2005 | Gordon |
| 2005/0228391 | A1 | 10/2005 | Levy |
| 2005/0261683 | A1 * | 11/2005 | Veldhuizen ................ A61F 2/44 623/17.11 |
| 2005/0278036 | A1 | 12/2005 | leonard et al. |
| 2006/0004455 | A1 | 1/2006 | Leonard et al. |
| 2006/0041258 | A1 | 2/2006 | Galea |
| 2006/0085070 | A1 | 4/2006 | Kim |
| 2006/0142858 | A1 | 6/2006 | Colleran et al. |
| 2006/0224241 | A1 | 10/2006 | Butler et al. |
| 2006/0235423 | A1 | 10/2006 | Cantu |
| 2006/0247778 | A1 | 11/2006 | Ferree |
| 2007/0032791 | A1 | 2/2007 | Greenhalgh |
| 2007/0073398 | A1 | 5/2007 | Fabian et al. |
| 2007/0123986 | A1 | 5/2007 | Schaller |
| 2007/0173939 | A1 | 7/2007 | Kim et al. |
| 2007/0233245 | A1 | 10/2007 | Trieu et al. |
| 2007/0260314 | A1 | 11/2007 | Biyani |
| 2007/0282449 | A1 | 12/2007 | de Villiers |
| 2008/0119853 | A1 | 5/2008 | Felt et al. |
| 2008/0125865 | A1 | 5/2008 | Abdelgany |
| 2008/0243255 | A1 | 10/2008 | Butler et al. |
| 2008/0249628 | A1 | 10/2008 | Altarac |
| 2008/0312743 | A1 | 12/2008 | Vila et al. |
| 2009/0093882 | A1 | 4/2009 | Oh |
| 2009/0157186 | A1 | 6/2009 | Magerl |
| 2009/0216274 | A1 | 8/2009 | Morancy-Meister et al. |
| 2009/0270873 | A1 | 10/2009 | Fabian |
| 2009/0299478 | A1 | 12/2009 | Carls et al. |
| 2010/0131009 | A1 | 5/2010 | Roebling et al. |
| 2010/0194753 | A1 | 8/2010 | Robotham et al. |
| 2010/0211176 | A1 | 8/2010 | Greenhalgh |
| 2010/0256764 | A1 | 10/2010 | Tsuang et al. |
| 2010/0286787 | A1 | 11/2010 | Villiers et al. |
| 2011/0054537 | A1 | 3/2011 | Miller |
| 2011/0125270 | A1 | 5/2011 | Paul |
| 2011/0138948 | A1 | 6/2011 | Jimenez |
| 2011/0172710 | A1 | 7/2011 | Thommen |
| 2011/0276141 | A1 * | 11/2011 | Caratsch ................ A61F 2/4455 623/17.16 |

(56) References Cited

U.S. PATENT DOCUMENTS

| | | | |
|---|---|---|---|
| 2012/0004732 A1* | 1/2012 | Goel | A61F 2/4455 623/17.16 |
| 2012/0025941 A1 | 2/2012 | Blackwell et al. | |
| 2012/0053642 A1 | 3/2012 | Lozier | |
| 2012/0083888 A1 | 4/2012 | Purcell et al. | |
| 2012/0123546 A1 | 5/2012 | Medina | |
| 2012/0165944 A1 | 6/2012 | McGuckin, Jr. | |
| 2012/0209386 A1* | 8/2012 | Triplett | A61F 2/4465 623/17.16 |
| 2012/0221107 A1* | 8/2012 | Sack | A61F 2/442 623/17.16 |
| 2012/0259416 A1* | 10/2012 | Blackwell | A61F 2/4455 623/17.16 |
| 2012/0271422 A1 | 10/2012 | Miller et al. | |
| 2012/0277866 A1* | 11/2012 | Kalluri | A61F 2/442 623/17.16 |
| 2013/0041471 A1* | 2/2013 | Siegal | A61F 2/442 623/17.16 |
| 2013/0007988 A1 | 3/2013 | Butler et al. | |
| 2013/0066374 A1 | 3/2013 | Gateey et al. | |
| 2013/0079883 A1 | 3/2013 | Butler et al. | |
| 2013/0144391 A1* | 6/2013 | Siegal | A61F 2/442 623/17.16 |
| 2013/0158664 A1 | 6/2013 | Palmatier et al. | |
| 2013/0158669 A1 | 6/2013 | Sungarian et al. | |
| 2013/0190876 A1* | 7/2013 | Drochner | A61F 2/442 623/17.16 |
| 2013/0027488 A1 | 10/2013 | McLuen et al. | |
| 2013/0274883 A1 | 10/2013 | McLuen et al. | |
| 2013/0317615 A1 | 11/2013 | Jimenez et al. | |
| 2013/0325128 A1 | 12/2013 | Perloff et al. | |
| 2014/0018822 A1 | 1/2014 | Dmuschewsky | |
| 2014/0052254 A1 | 2/2014 | Glerum et al. | |
| 2014/0114429 A1 | 4/2014 | Slone et al. | |
| 2014/0156007 A1 | 6/2014 | Pabst et al. | |
| 2014/0188224 A1* | 7/2014 | Dmuschewsky | A61F 2/442 623/17.16 |
| 2014/0243982 A1 | 8/2014 | Miller | |
| 2014/0249628 A1 | 9/2014 | Weiman | |
| 2014/0249629 A1 | 9/2014 | Moskowitz | |
| 2014/0277139 A1* | 9/2014 | Vrionis | A61B 17/70 606/246 |

FOREIGN PATENT DOCUMENTS

| | | |
|---|---|---|
| DE | 4416605 | 6/1995 |
| FR | 2717068 | 9/1995 |
| JP | 2004530527 | 10/2004 |
| JP | 2008512218 | 4/2008 |
| JP | 2011120957 | 6/2011 |
| WO | 98/34552 | 8/1998 |
| WO | 03003951 | 1/2003 |
| WO | 03005276 | 1/2003 |
| WO | 2003003951 | 1/2003 |
| WO | 2006050500 | 5/2006 |
| WO | 20060050500 | 5/2006 |
| WO | 2007073584 | 7/2007 |
| WO | 2008044057 | 4/2008 |
| WO | 2008084479 | 7/2008 |
| WO | 2008103781 | 8/2008 |
| WO | 2012011078 | 7/2011 |
| WO | 2012117312 | 9/2012 |
| WO | 2013052807 | 4/2013 |
| WO | 2013/133729 | 9/2013 |
| WO | 20130133729 | 9/2013 |
| WO | 2013158294 | 10/2013 |
| WO | 20130158294 | 10/2013 |
| WO | 2014091029 | 6/2014 |

* cited by examiner

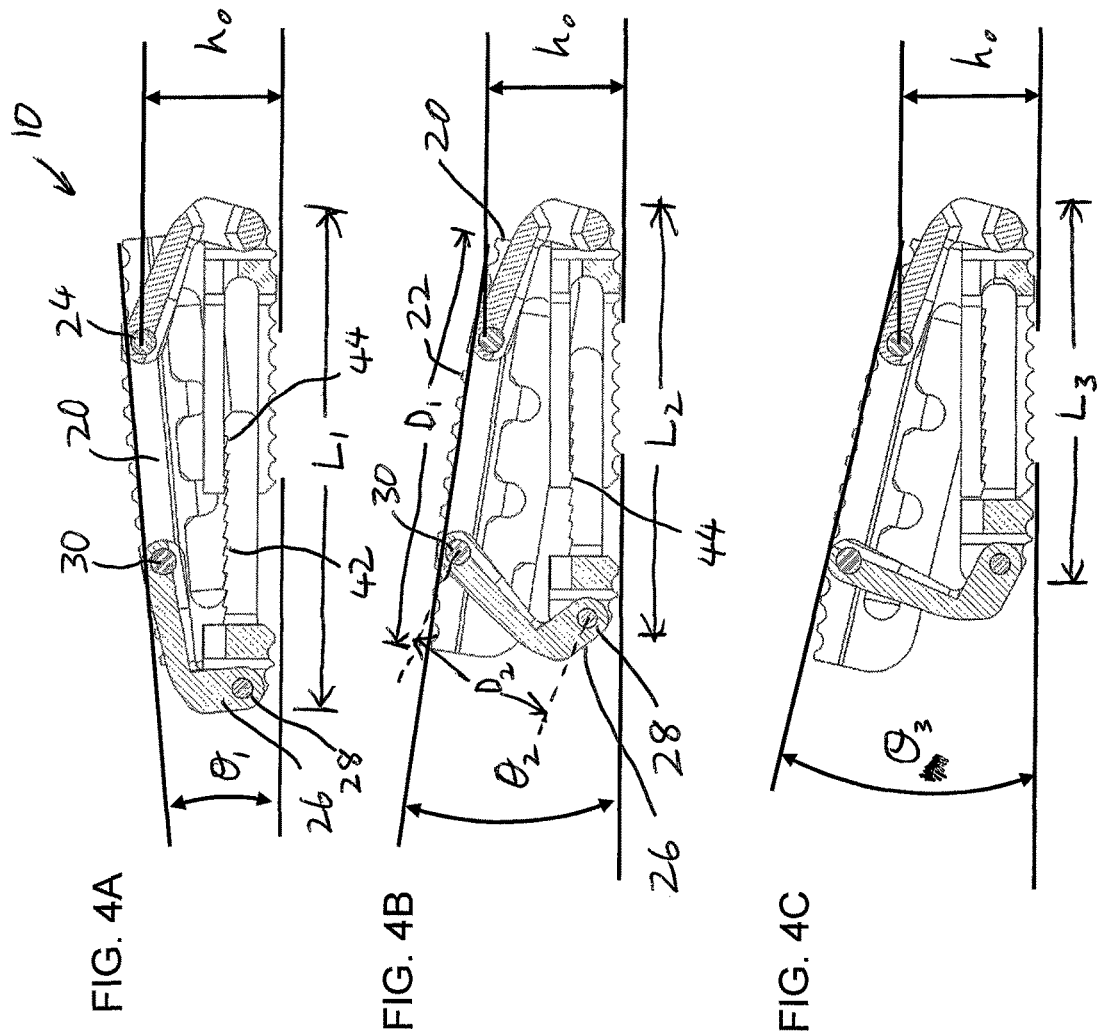

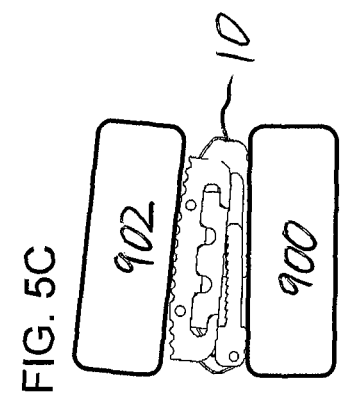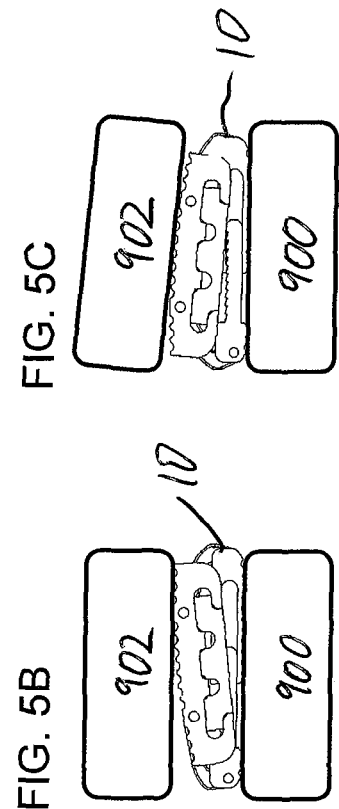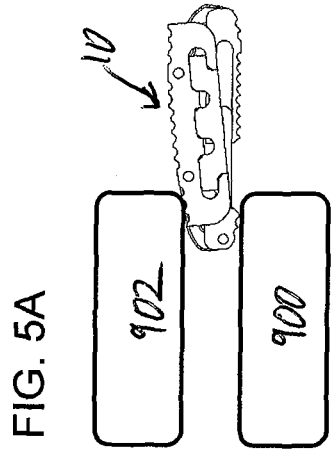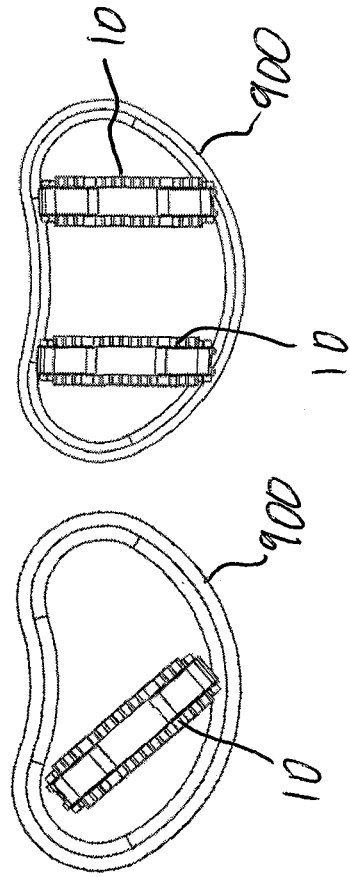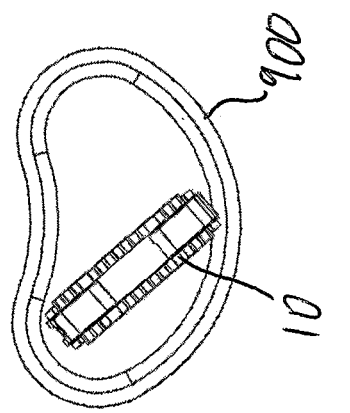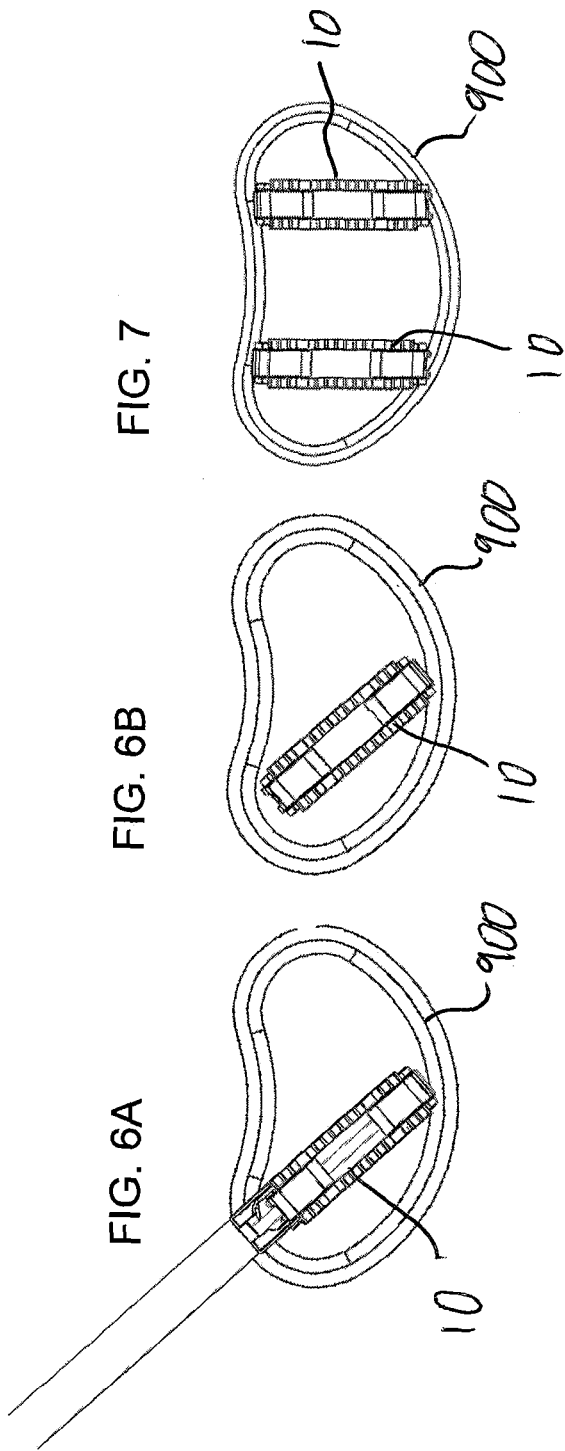

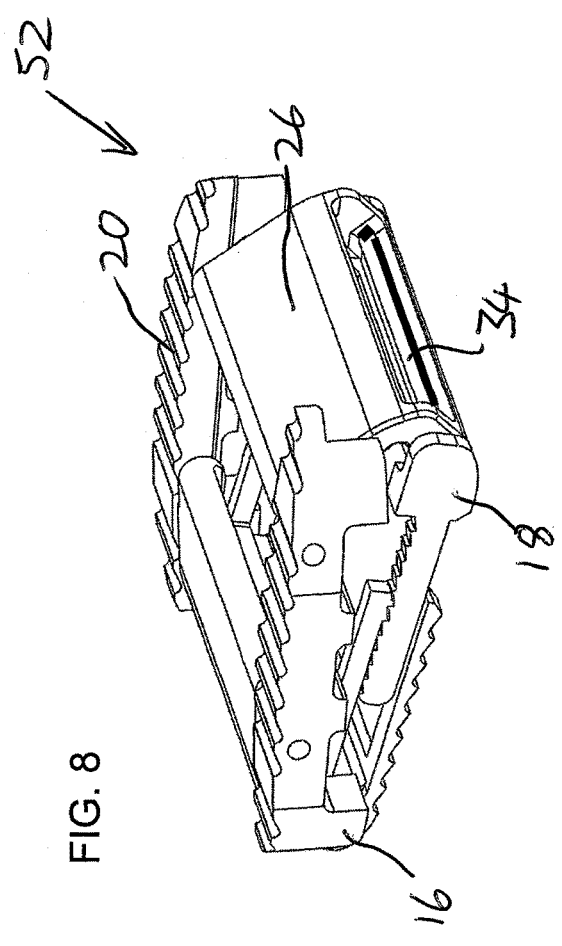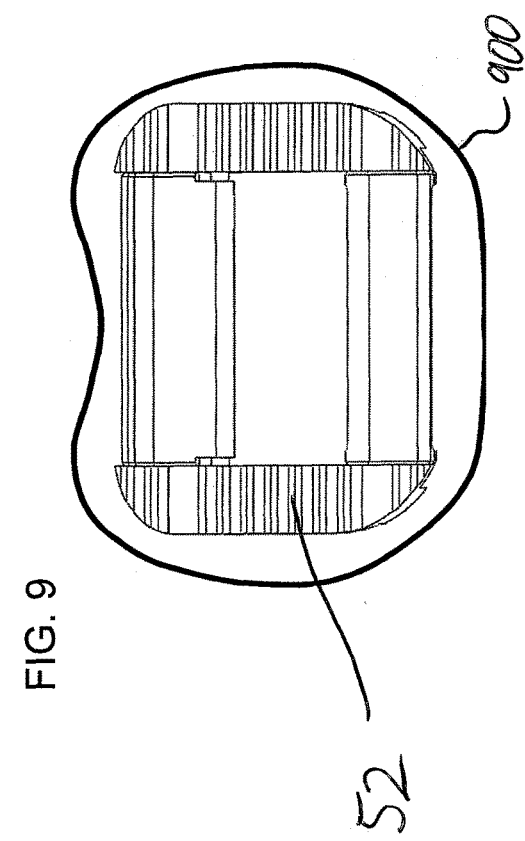
FIG. 8
FIG. 9

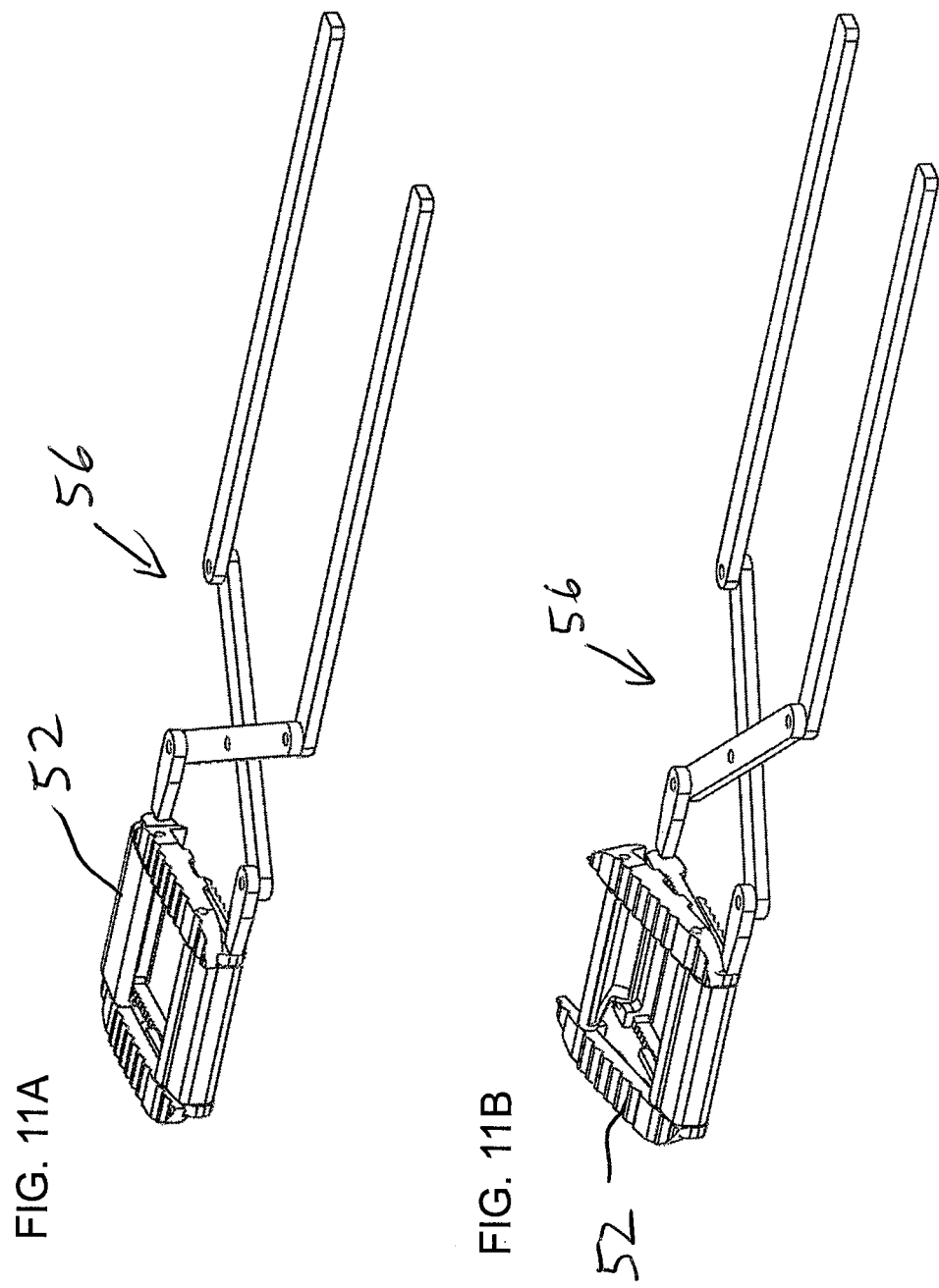

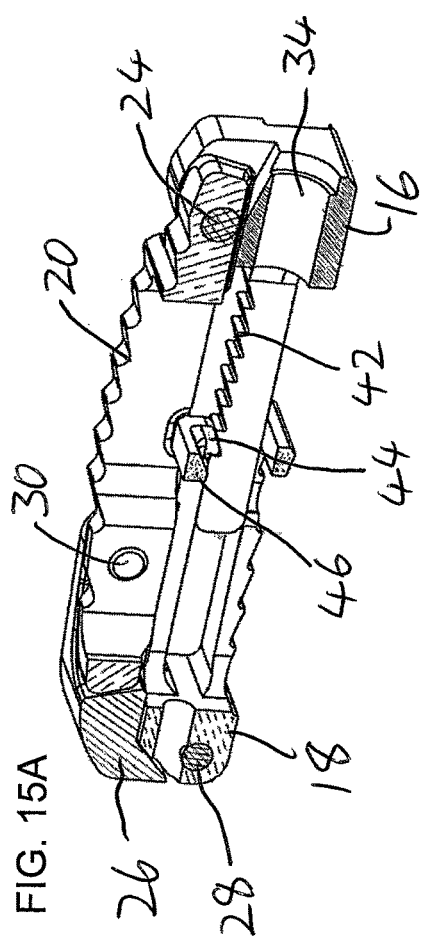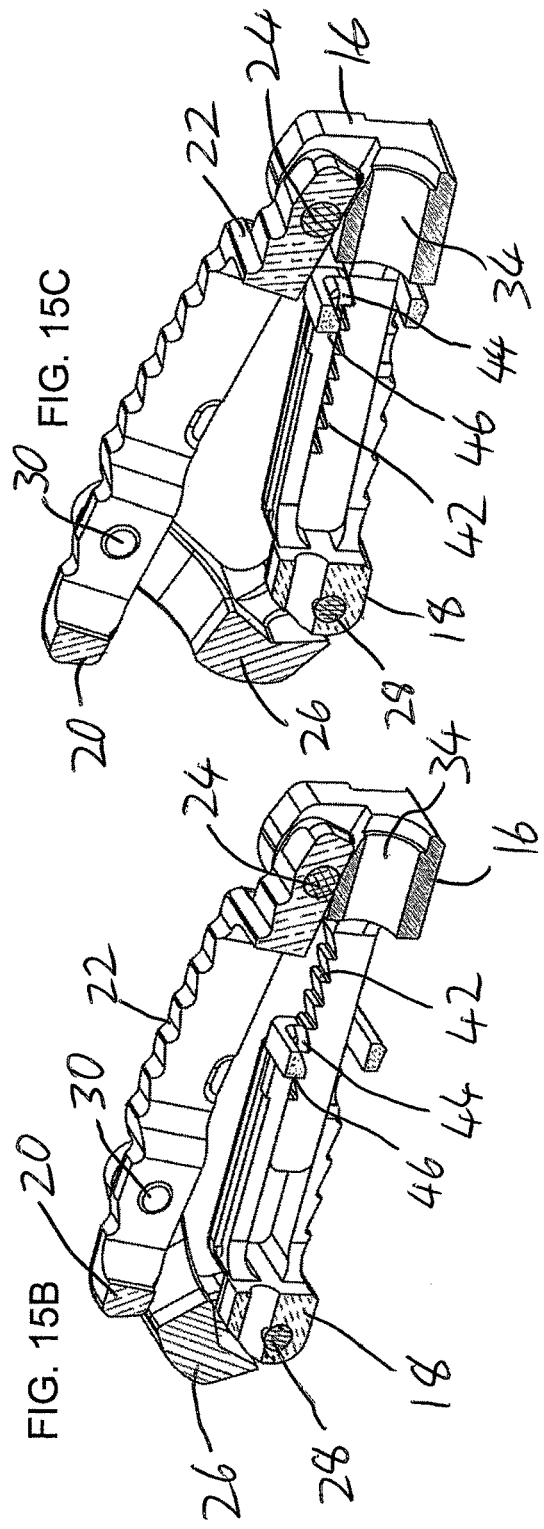

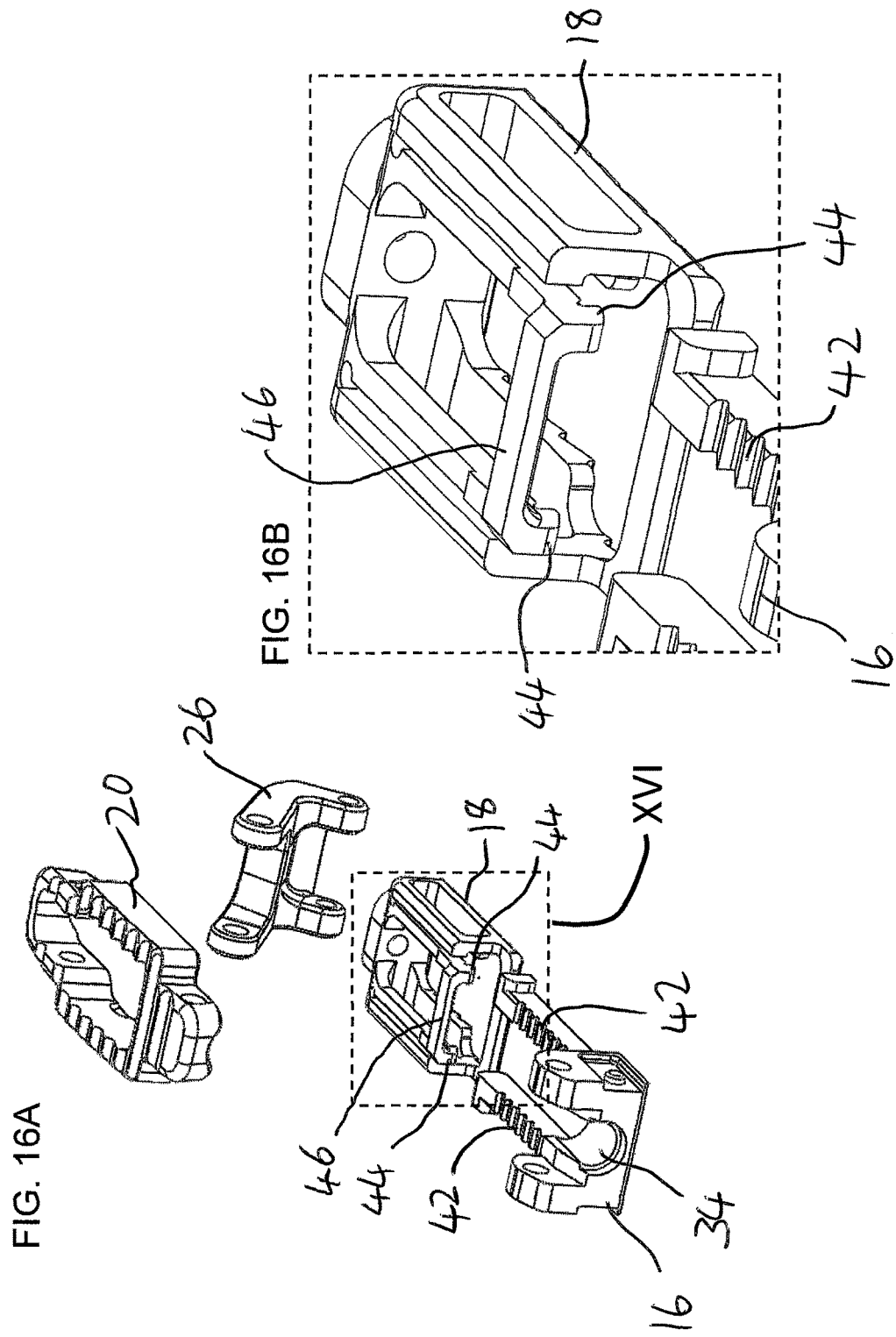

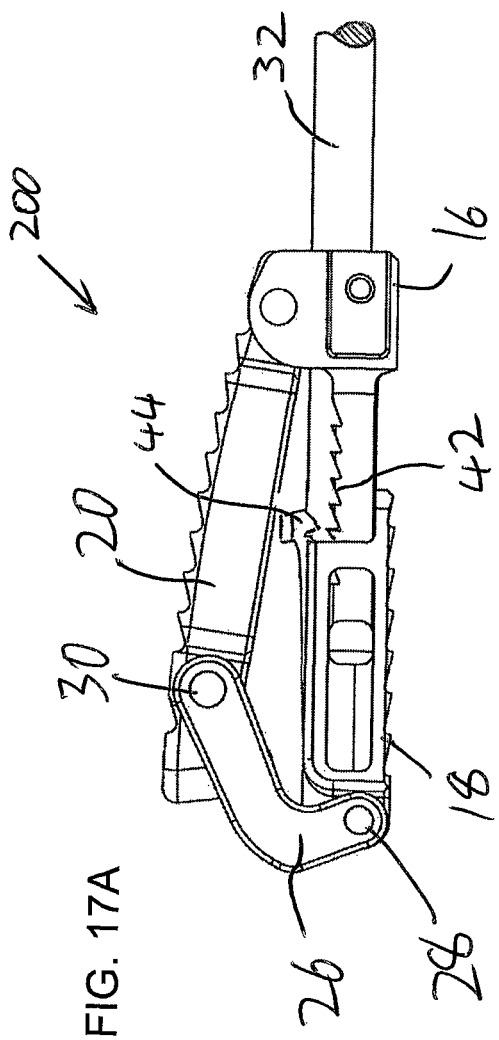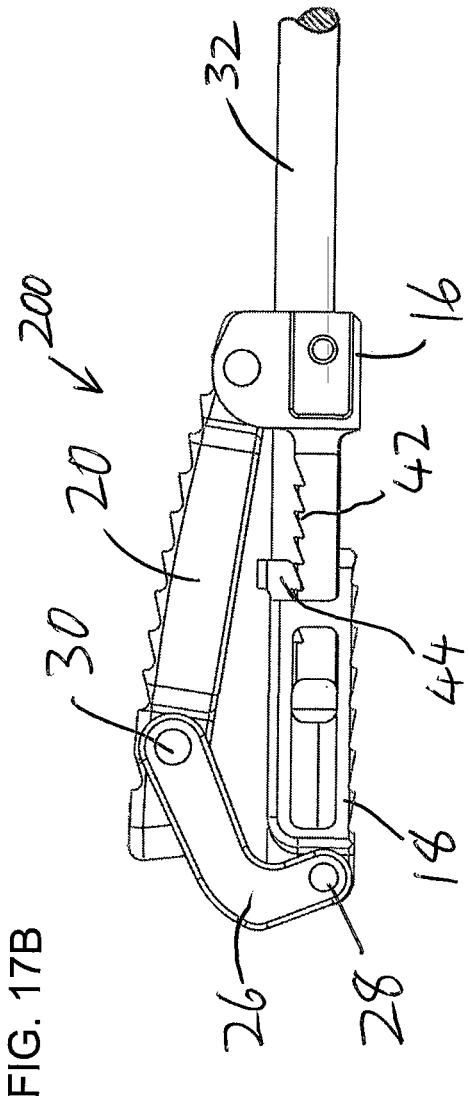
FIG. 17A
FIG. 17B

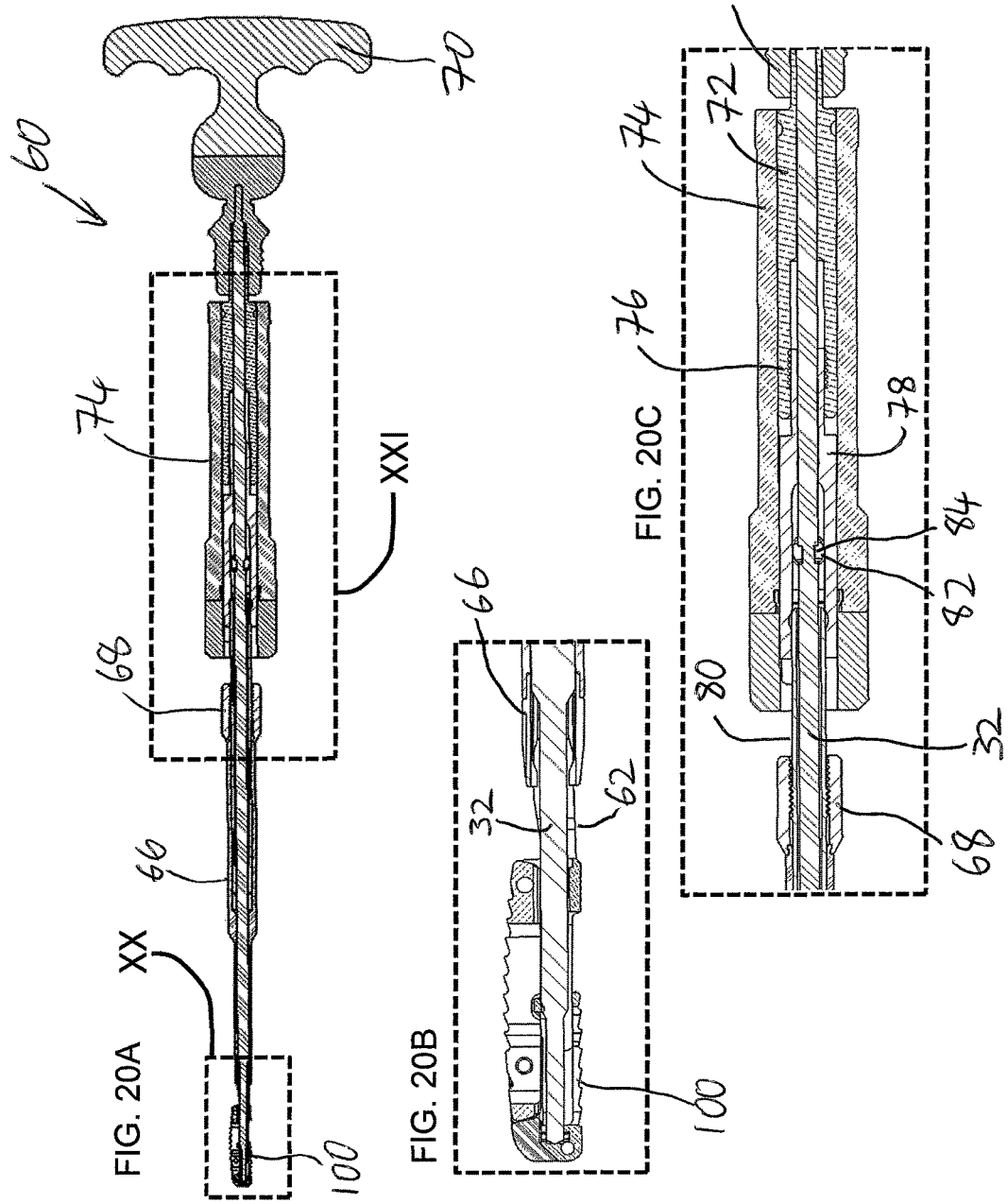

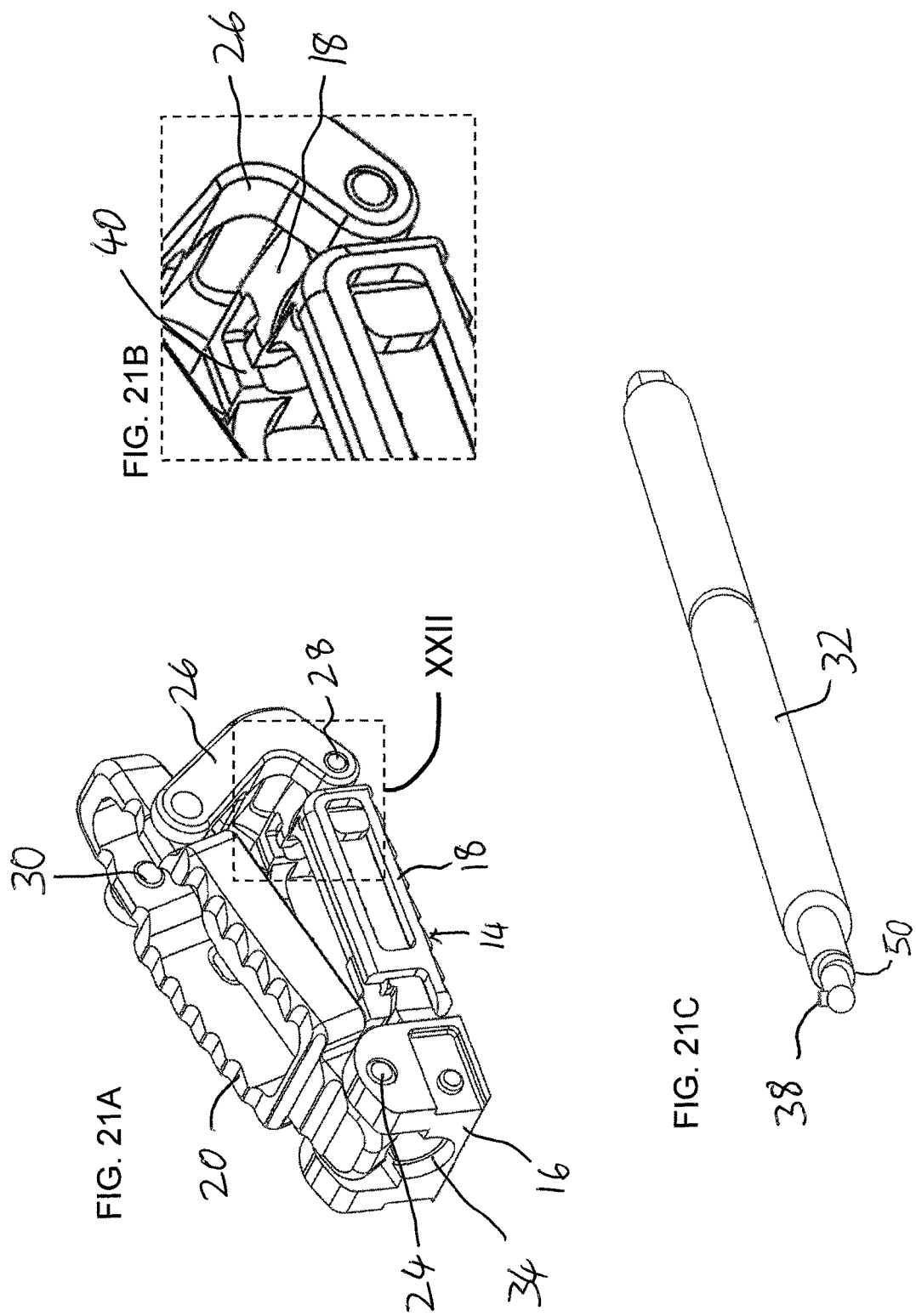

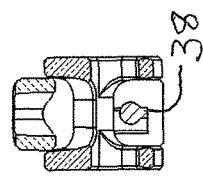
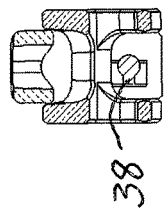
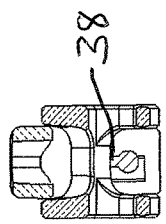
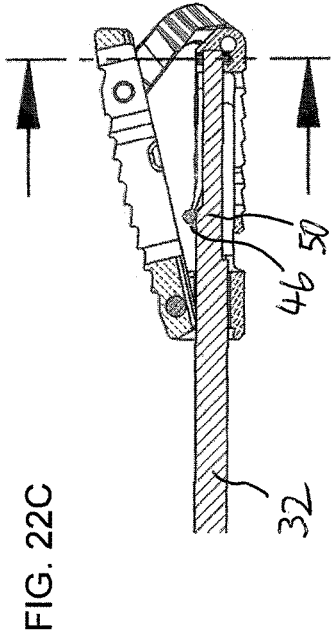
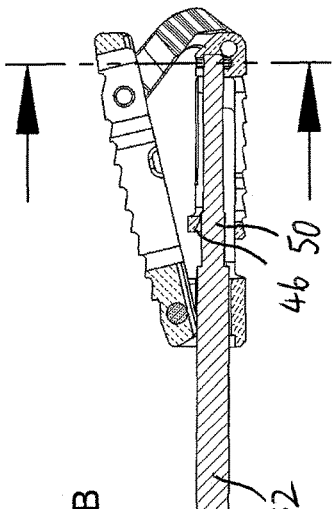
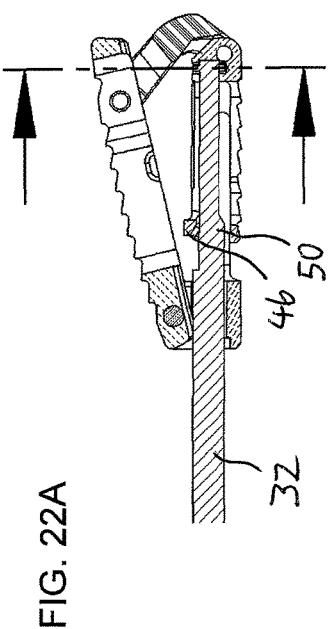

ORTHOPEDIC IMPLANT WITH ADJUSTABLE ANGLE BETWEEN TISSUE CONTACT SURFACES

FIELD AND BACKGROUND OF THE INVENTION

The present invention relates to orthopedic implants and, in particular, it concerns an orthopedic implant with an adjustable angle between two tissue contact surfaces.

It is known to deploy implants between tissue surfaces in a range of orthopedic procedures, and in various cases, it may be advantageous to use an implant to modify an angular relation between the tissue surfaces. By way of non-limiting example, this need may occur in spinal surgery, such as where there is a need for restoration of a lordotic angle between vertebrae, or to correct scoliosis misalignment between vertebrae.

In certain cases, it may be possible to adjust an angle between tissue contact surfaces after an implant is positioned within the body. An example of a device for performing such an adjustment is U.S. Pat. No. 6,190,414 to Young et al.

There is therefore a need for an orthopedic implant with an adjustable angle between two tissue contact surfaces.

SUMMARY OF THE INVENTION

The present invention is an orthopedic implant with an adjustable angle between two tissue contact surfaces According to the teachings of the present invention there is provided, an implant for insertion between two regions of tissue, the implant comprising: (a) a base having a first contact surface for contacting a first region of tissue, the base comprising a first portion displaceable relative to a second portion, the base assuming an initial length and being shortened towards a second length when the first portion is displaced towards the second portion; (b) a hinged element having a second contact surface for contacting a second region of tissue, the hinged element being interconnected with the first portion of the base at an effective hinge; and (c) a linking segment hingedly connected to both the second portion of the base and to the hinged element, such that shortening of the base from the initial length towards the second length causes the linking segment to push a region of the hinged element away from the base, thereby changing an angle of the second contact surface relative to the first contact surface, wherein the second contact surface has a largest dimension referred to as a contact surface length, and wherein the linking segment has a dimension between axes of the hinged connection referred to as a linking segment length, the contact surface length being at least 40% longer than the linking segment length.

According to an additional, or alternative, feature of certain embodiments of the present invention, the hinged element has an end corresponding to a point on the hinged element furthest from the effective hinge, and wherein a location of hinged connection between the linking segment and the hinged element is distanced from the end by at least 10% of the contact surface length.

According to a further feature of certain embodiments of the present invention, there is also provided a deployment rod inserted via an opening in a proximal end of the implant and engaging a distal one of the first and second portions of the base such that a force applied to the proximal end of the implant in a distal direction can be opposed by a counter-force applied to the deployment rod, thereby causing shortening of the base.

According to a further feature of certain embodiments of the present invention, the first portion and the second portion are formed with complementary features defining a ratchet configuration comprising a series of ratchet teeth and a resiliently biased detent, the ratchet configuration being deployed to allow shortening of the base from the initial length through a range of lengths, and to oppose lengthening of the base.

According to a further feature of certain embodiments of the present invention, there is also provided a ratchet release element insertable via an opening in the implant and deployable to release engagement of the detent with the ratchet teeth to allow lengthening of the base.

According to a further feature of certain embodiments of the present invention, there is also provided a deployment rod inserted via an opening in a proximal end of the implant and engaging a distal one of the first and second portions of the base such that a force applied to the proximal end of the implant in a distal direction can be opposed by tension applied to the deployment rod, thereby causing shortening of the base.

According to a further feature of certain embodiments of the present invention, an engagement of the deployment rod with the distal portion is configured to allow a first motion of the deployment rod while maintaining engagement with the distal portion, and wherein the deployment rod has at least one feature deployed such that the first motion is effective to bring the at least one feature to bear on a part of the ratchet configuration so as to release engagement of the detent with the ratchet teeth to allow lengthening of the base.

According to a further feature of certain embodiments of the present invention, the engagement of the deployment rod with the distal portion is a threaded engagement, and wherein the first motion is a rotation effective to advance the deployment rod in relation to the threaded engagement.

According to a further feature of certain embodiments of the present invention, the first contact surface and the second contact surface are each partial surfaces having one or more openings totaling at least a quarter of a total area of a contact surface footprint.

According to a further feature of certain embodiments of the present invention, the first contact surface defines a first contact plane and the second contact surface defines a second contact plane, and wherein shortening of the base from the initial length towards the second length displaces the second contact plane through an angular range of at least 10° relative to the first contact plane.

There is also provided according to the teachings of certain embodiments of the present invention, a method comprising the steps of: (a) introducing an implant according to the invention between two vertebral bodies such that the first contact surface contacts an endplate of a first of the vertebral bodies and the second contact surface contacts an endplate of a second of the vertebral bodies; and (b) causing relative motion of the first and second portions of the base so as to change an angle between the first and second contact surfaces, thereby changing an angle between the endplates.

According to a further feature of certain embodiments of the present invention, the introducing and the causing relative motion are performed so as to correct a scoliosis misalignment between adjacent vertebral bodies.

According to a further feature of certain embodiments of the present invention, the introducing and the causing relative motion are performed so as to restore or increase an angle of lordosis between adjacent vertebral bodies.

There is also provided according to the teachings of certain embodiments of the present invention, a method comprising the steps of: (a) introducing two implants, each according to the invention, between two vertebral bodies such that the first contact surface of each of the implants contacts an endplate of a first of the vertebral bodies and the second contact surface of each of the implants contacts an endplate of a second of the vertebral bodies; and (b) for each of the implants, causing relative motion of the first and second portions of the base so as to change an angle between the first and second contact surfaces, thereby changing an angle between the endplates.

BRIEF DESCRIPTION OF THE DRAWINGS

The invention is herein described, by way of example only, with reference to the accompanying drawings, wherein:

FIGS. 4A-4C are center-plane cross-sectional views taken through the implant of FIG. 1A in a minimum-angle, intermediate-angle and maximum-angle state, respectively;

FIGS. 5A-5C are a sequence of schematic lateral views illustrating a process of restoration of lordotic angle between adjacent vertebral bodies using the implant of FIGS. 1A and 1B;

FIG. 6A is a schematic axial view illustrating introduction of the implant of FIG. 1A into an intervertebral space via a transforaminal approach;

FIG. 6B is a view similar to FIG. 6A after deployment of the implant;

FIG. 7 is a schematic axial view illustrating a pair of implants as in FIG. 1A deployed bilaterally in an intervertebral space via a posterior approach;

FIG. 8 is an isometric view of a variant of the implant of FIG. 1A suitable for intervertebral placement via an anterior or lateral approach;

FIG. 9 is a schematic axial view illustrating placement of the implant of FIG. 8 within an intervertebral space;

FIGS. 11A and 11B are schematic isometric views of the implant of FIG. 8 held by a compression tool for deployment via a lateral approach, the implant being shown in a minimum-angle and an increased-angle state, respectively;

FIGS. 15A-15C are isometric views similar to FIGS. 14A-14C, respectively, cut-away along a center-plane of the implant;

FIG. 16A is an isometric exploded view illustrating the components of the implant of FIG. 14A;

FIG. 16B is an enlarged view of the region of FIG. 16A designated XVI;

FIG. 17A is a side view of the implant of FIG. 14B showing the implant in a partially raised state engaged by a deployment rod with an integrated ratchet release element effective to release locking of a ratchet configuration;

FIG. 17B is a view similar to FIG. 17A during removal of the deployment rod, and showing the ratchet configuration engaged;

FIG. 20A is a center-plane cross-sectional view taken through the delivery system as illustrated in FIG. 19A;

FIG. 20B is an enlarged view of the region of FIG. 20A designated XX;

FIG. 20C is an enlarged view of the region of FIG. 20A designated XXI;

FIG. 21A is an isometric view of a variant of the implant of FIG. 14A-14C employing a keyhole slot for engagement of a deployment rod;

FIG. 21B is an enlargement of a region of FIG. 21A designated XXI;

FIG. 21C is an isometric view of a deployment rod for use with the implant of FIG. 21A including a keyhole slot engagement configuration and a cam-type ratchet mechanism release feature;

FIGS. 22A-22C are central-plane cross-sectional views taken through the implant of FIG. 21A showing the deployment rod in a pre-engagement state, an engaged ratchet-release state and an engaged ratchet-engaged state, respectively;

FIGS. 23A-23C are cross-sectional views taken along the plane XXIII shown in FIGS. 22A-22C, respectively;

DESCRIPTION OF THE PREFERRED EMBODIMENTS

Figure 1A:
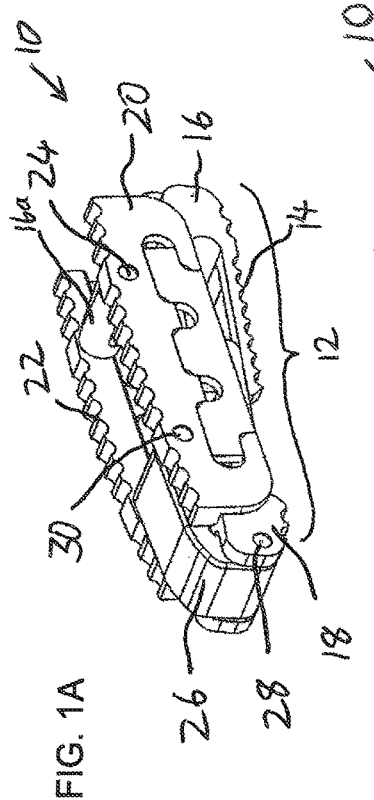
FIGS. 1A and 1B are isometric views of an implant, constructed and operative according to an embodiment of the present invention, with an adjustable angle between two tissue contact surfaces, the implant being shown in a minimum-angle and an increased-angle state, respectively.
Figure 1B:
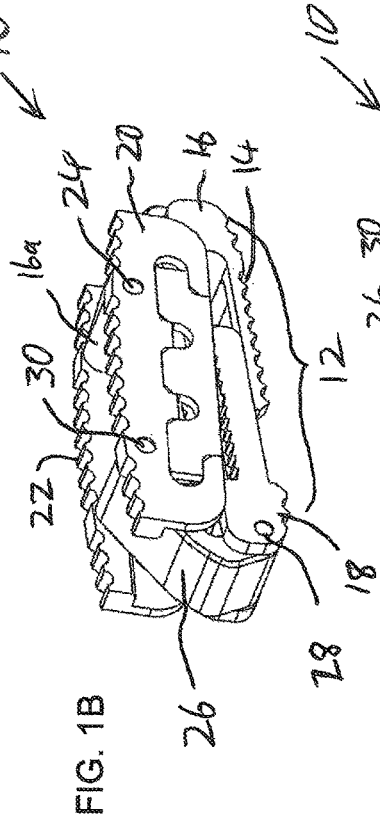
Figure 1C:
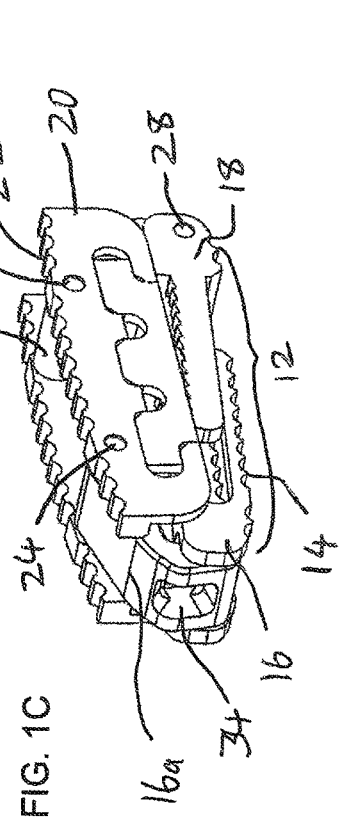
FIG. 1C is an isometric view similar to FIG. 1B from a proximal side of the implant.
Figure 2A:
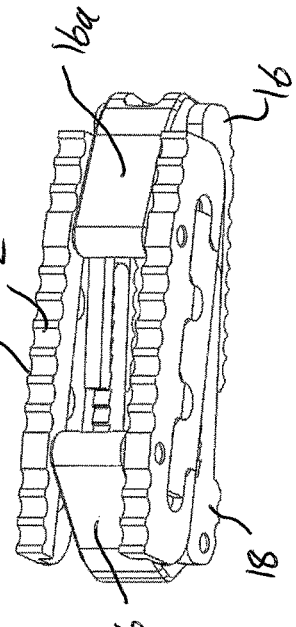
FIGS. 2A and 2B are additional isometric views corresponding to FIGS. 1A and 1B, respectively, taken from above the implant.
Figure 2B:
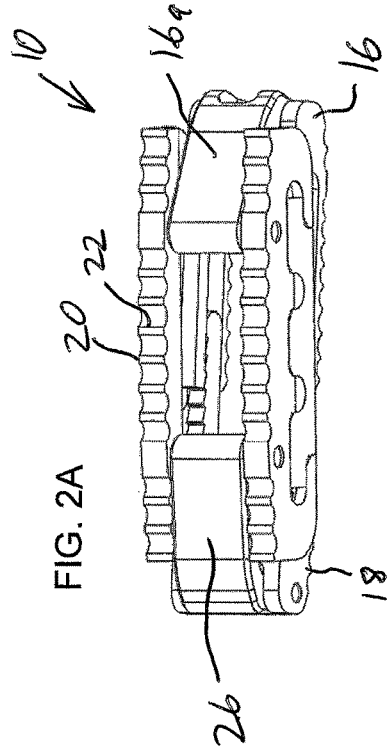

The present invention is an orthopedic implant with an adjustable angle between two tissue contact surfaces.

The principles and operation of implants according to the present invention may be better understood with reference to the drawings and the accompanying description.

Referring now to the drawings, FIGS. 1A-25B illustrate various embodiments of an implant, constructed and operative according to the teachings of an embodiment of the present invention.

Overview

Referring collectively to all of the embodiments, there is shown an implant, for insertion between two regions of tissue, having a base 12 having a first contact surface 14 for contacting a first region of tissue. Base 12 includes a first portion 16 displaceable relative to a second portion 18 so that base 12 assuming an initial length, and is shortened towards a second length when first portion 16 is displaced towards second portion 18. A hinged element 20, having a second contact surface 22 for contacting a second region of tissue, is interconnected with first portion 16 of base 12 at an effective hinge 24. A linking segment 26 is hingedly connected to both second portion 18 of base 12 at a hinge 28 and to hinged element 20 at a hinge 30.

The structure and deployment of linking segment 26 is such that shortening of base 12 from its initial length towards its second length causes the linking segment to push a region of hinged element 20 away from base 12, thereby changing an angle of second contact surface 22 relative to first contact surface 14.

At this stage, it will already be appreciated that the present invention provides a highly advantageous solution for adjusting the angular relation between tissue surfaces. In a first particularly preferred set of implementations and corresponding applications, the device is deployed in an intervertebral space and actuated to restore a desired degree of lordosis, or in some cases to generate a hyperlordotic adjustment, as will be discussed further below. In other applications, the device may be oriented to allow adjustment of a lateral misalignment between vertebrae, such as for correction of a scoliosis misalignment. The device preferably provides a continuous, or near continuous, range of adjustment, typically spanning a range (from minimum angle to maximum angle) of at least 10 degrees. In some implementations, adjustments reaching angles in excess of 30 degrees may be provided. These and other features of the invention will become clearer from the following description and with reference to the accompanying drawings.

It should be appreciated that the various exemplary embodiments of the present invention described below are closely analogous in structure and function. For conciseness of presentation, features described in the context of one embodiment will not be described again in the context of another embodiment, and should be understood to apply equally to all embodiments unless explicitly stated or clearly evident to the contrary. For example, various forms of deployment and corresponding methods described with reference to FIGS. 5A-13C, and an exemplary delivery system described with reference to FIGS. 19A-20C, are not limited to the details of the implant embodiments with which they are illustrated, and should be understood to be applicable to all embodiments of the present invention disclosed herein, with any minor adaptations that would be required, as will be clear to a person ordinarily skilled in the art.

Definitions

Before addressing the features of the invention in more detail, it will be helpful to define certain terminology as used herein in the description and claims. Where reference is made to various elements, such as base 12, hinged element 20 and linking segment 26, it should be appreciated that each element may in fact be made up of various subcomponents, rigidly or flexibly interconnected. With the exception of first and second portions 16, 18 of base 12 which are explicitly referred to as being relatively movable, other subdivisions of the above components into subcomponents are most preferably rigidly interconnected such that they function mechanically as a single component. Thus, by way of example, in the embodiment of FIG. 1A, first portion 16 of base 12 is rigidly interconnected with a bridging portion 16a which supports hinge 24, while hinged element 20 is formed from two elongated components interconnected by the pins of hinges 24 and 30.

Reference is made to various "contact surfaces" for contacting tissue, and to angles formed between such contact surfaces. As will be clear from the various embodiments shown herein, the contact surfaces are typically not smooth surfaces, but rather are formed with various textures and/or tissue engaging features which facilitate anchoring of the device against the adjacent tissue surfaces, typically bone. Furthermore, the overall profile of the contact surface may have a curvature, such as a convex curvature to engage a corresponding concavity, for example, in a lumbar vertebral endplate. In all such cases, a plane of the contact surface for the purpose of defining angles thereto is defined by a best-fit plane over the entire contact surface, for example by minimizing a least-squares misfit, neglecting localized projecting features. When reference is made to contact surface 14 of base 12, this includes the parts of both first and second portions 16 and 18 that are disposed to contact adjacent tissue, but excludes relatively recessed intermediate portions which are not typically expected to come in contact with adjacent tissue.

The angle between two contact surfaces is defined herein in the description and claims as the angle formed between the planes of the two contact surfaces when extrapolated to intersect, typically beyond the body of the implant. In a state in which the two contact surface planes are parallel, the angle between them is defined as zero. Where the end of hinged element 20 furthest from effective hinge 24 is initially closer to base 12 than the other end of hinged element 20, such as in FIGS. 1A and 4A, the angle is defined as negative.

As also clear from the various examples, the contact surfaces are typically not full surfaces but rather have various openings (apertures or spaces) which may be either enclosed or open-sided. In fact, in certain preferred implementations such as for spinal fusion, it is particularly preferred that the contact surface are partial surfaces having one or more openings totaling at least a quarter, and most preferably at least half, of a total area of a contact surface footprint. The "contact surface footprint" for this purpose is taken to be the region enclosed by the shortest line in the contact surface plane encompassing (the projections of) all parts of the contact surface.

Where reference is made to a length of the contact surface, this refers to the largest dimension of the contact surface footprint, exemplified by dimension $D_1$ in FIG. 4B.

Where reference is made to the length of linking segment 26, this refers to a dimension of the linking segment between axes 28, 30 of its hinged interconnection with base 12 and hinged element 20, as exemplified by dimension $D_2$ in FIG. 4B.

Where reference is made to an "effective hinge" or "hinged interconnection", this refers to both hinge joints, pivotal linkages and integral hinges which provide an effect similar to a single hinge over the relevant range of angular motion. It is a particular feature of certain preferred embodiments of the present invention that overall geometry of the axes, or effective axes, 24, 28 and 30 remains effectively a rigid triangular form with one variable-length side which generates the required change in form, although a linkage or integral joint which defines an effective axis which lies outside the body of the implant and/or which moves somewhat during the adjustment also falls within the scope of this definition.

It should be noted that any and all references to particular orientations of the devices of the present invention, to anatomical directions, or to motion of one component relative to another, are used merely for clarity of presentation, and do not limit the scope of the invention as claimed unless explicitly stated to the contrary. The devices may be used in any orientation including, for example, with "base 12" uppermost, and motion of first portion 16 towards second portion 18 typically refers to relative motion which may be achieved by moving either or both of the components in question.

The terms "proximal" and "distal" are used in their normal senses to relate to the portions of the device closer and further, respectively, from the medical practitioner during deployment of the device. In many of the exemplary embodiments, first portion 16 corresponds to the proximal portion and second portion 18 corresponds to the distal portion. This correspondence, however, is exemplary and should not be considered limiting. Reversed configurations also clearly fall within the scope of the present invention, for example, as illustrated with reference to an anterior approach implant in FIG. 10.

Geometrical Configurations

As mentioned above, a wide range of implementations of the present invention may essentially be viewed as a rigid triangular configuration defined by the positions of axes, or effective axes, 24, 28 and 30, wherein shortening of one side of the triangle, corresponding to at least part of base 12, causes a change in angle of hinged element 20, associated with one of the other sides of the triangle, relative to the base. Within this general definition, the specific positions of the axes, relative sizes of the sides, and geometrical forms of the contact surfaces relative to the underlying triangle, may all vary considerably according to the intended application, the required range of angles, the expected loading, the available deployment forces, and the properties of the materials to be used. A partial set of examples of possible geometries is presented in the examples described herein.

In one subset of implementations, referring to terminology illustrated in FIGS. 4A-4C, the contact surface length $D_1$ of hinged element 20 is at least 40% longer than the linking segment length $D_2$, and in many cases 100% longer, i.e., where $D_1$ is at least twice $D_2$. This ratio reflects the fact that hinged element 20 performs a function of supporting tissue whereas linking segment 26 provides only an internal mechanical support function, leading to asymmetry between elements 20 and 26. Furthermore, in a range of applications, it may be preferable that a "fully raised" state of linking segment 26, corresponding to the fully shortened state of base 12, has the axis-to-axis direction of linking segment 26 deployed at a steep angle, typically in excess of 70 degrees, to a plane of base 12.

The contact surface length $D_1$ of hinged element 20 is also typically at least 80% of the minimum length $L_3$ of base 12, and in various cases, at least equal to $L_3$.

A further parameter which may vary between implementations is the position of hinged connection 30 along hinged element 20. In certain implementations, hinged connection 30 is located closely adjacent to (i.e., within 10% of the contact surface length from) the end of hinged element 20 furthest from effective hinge 24. In various cases, it may be advantageous to place hinged connection 30 closer to effective hinge 24, thereby typically achieving an increased range of angular adjustment for a given adjustment of the length of base 12. For this reason, a preferred position of hinged connection 30 for certain implementations of the present invention is specifically distanced from the end of hinged element 20 by at least 10% of the contact surface length.

Figure 26A:
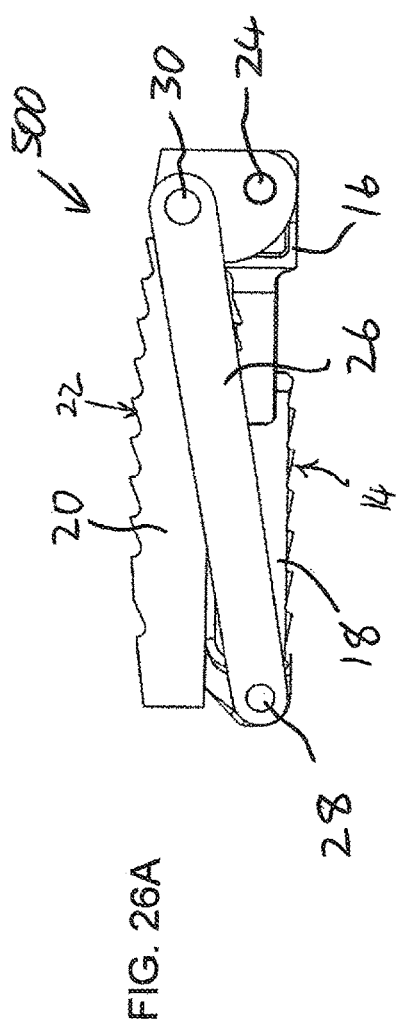
FIGS. 26A and 26B are side views of an implant according to a still further variant implementation of the implant of FIG. 14A illustrating a further alternative deployment of a linking segment, the implant being shown in a minimum angle and maximum angle state, respectively.
Figure 26B:
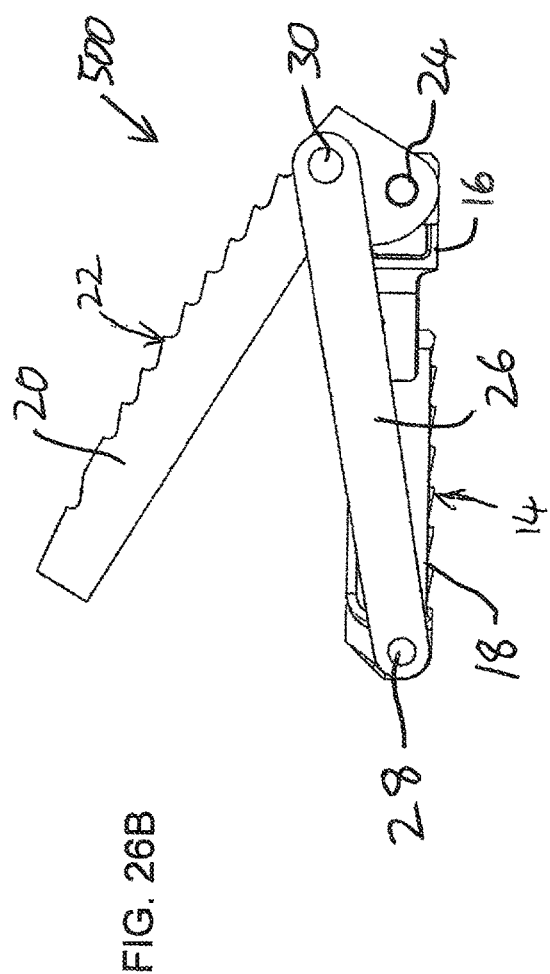

By way of examples, in a preferred but non-limiting examples of implant 10 illustrated with reference to FIGS. 1A-4C and an implant 200 illustrated with reference to FIGS. 14A-18B, hinged connection 30 is located between 10% and 30% of the contact surface length from the end. In a preferred but non-limiting example of an implant 300 illustrated in FIGS. 24A and 24B, hinged connection 30 is located between 30% and 60% of the contact surface length from the end. In a further preferred but non-limiting example of an implant 400 illustrated in FIGS. 25A and 25B, hinged connection 30 is located between 50% and 80% of the contact surface length from the end furthest from effective hinge 24. In a still further preferred but non-limiting example of an implant 500 illustrated in FIGS. 26A and 26B, hinged connection 30 is located between 80% and 100% of the contact surface length from the end furthest from effective hinge 24, while effective hinge 24 itself is moved closer to contact surface 14 of the base to ensure the required leverage to pivot hinged element 20 when the length of the base changes.

The latter options (particularly implants 400 and 500) facilitate achieving a given angular adjustment with much smaller relative motion between first and second portions 16, 18 of base 12 and/or can achieve much greater ranges of angular adjustment, for example, providing angles up to in excess of 40 degrees for hyperlordotic correction where desired. The increased ratio of output angular motion subjects the components to significantly greater mechanical stress than the earlier embodiments, therefore requiring use of strong mechanical materials and/or more robust structural design. A typical, non-limiting example of material suitable for manufacturing various embodiments of the present invention, including such high-stress implants, is titanium. An additional material more suited for the lower-stress implementations is a biocompatible structural polymer, such as PEEK.

Actuation Mechanisms and Locking Mechanisms

Angular adjustment of the implants of the present invention is preferably achieved by shortening base 12, i.e., by bringing first portion 16 and second portion 18 towards each other, referred to herein as "actuation". In most cases, after actuation, it is desired to maintain an angled state of the implant, typically at or near the final raised state which the implant achieved during adjustment. This is referred to herein as "locking". The functions of actuation and locking may be performed by a single combined mechanism, or by separate mechanisms dedicated to each function, and such mechanisms may be either integrated into the implant structure or may be separate structures which are deployable within the implant prior to use and/or removable from the implant after use, as appropriate.

By way of one non-limiting example of a combined, integrated actuation and locking mechanism, a threaded actuator (not shown) may be deployed so as to link first and second portions 16, 18 so that rotation of an actuator bolt, or of a tightening nut, is effective to apply force to bring the two portions together, thereby shortening base 12. A threaded actuator with a suitably chosen thread pitch also achieves frictional locking, thereby maintaining any desired final angle of the device. A threaded actuator is particularly suited to high stress implementations such as implants 400 and 500 discussed above.

In an alternative particularly preferred but non-limiting set of implementations, a removable actuating mechanism is employed, most preferably integrated with a delivery system for positioning the implant within a body. An example of such a system is illustrated in FIGS. 19A-20C.

A preferred principle of operation for a removable actuation system employs a deployment rod 32 (FIGS. 17A-18B and 20A-20C) which is inserted via an opening 34 in a proximal end of the implant, here corresponding to first portion 16, and engages a distal portion, here corresponding to second portion 18. As a result of this engagement, a force applied to a proximal end of the implant, in this case first portion 16, in a distal direction can be opposed by a counterforce applied via deployment rod 32 to second portion 18, thereby causing shortening of base 12.

Figure 18A:
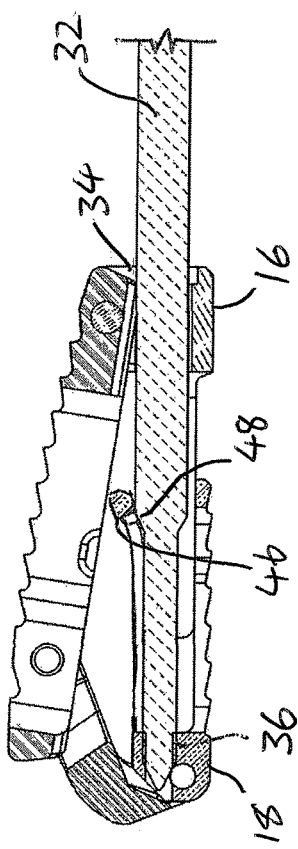
FIGS. 18A and 18B are central-plane cross-sectional views taken through FIGS. 17A and 17B, respectively.
Figure 18B:
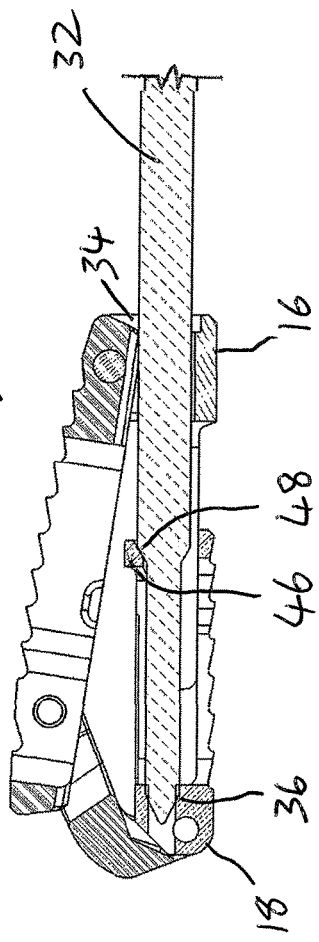
Figure 19A:
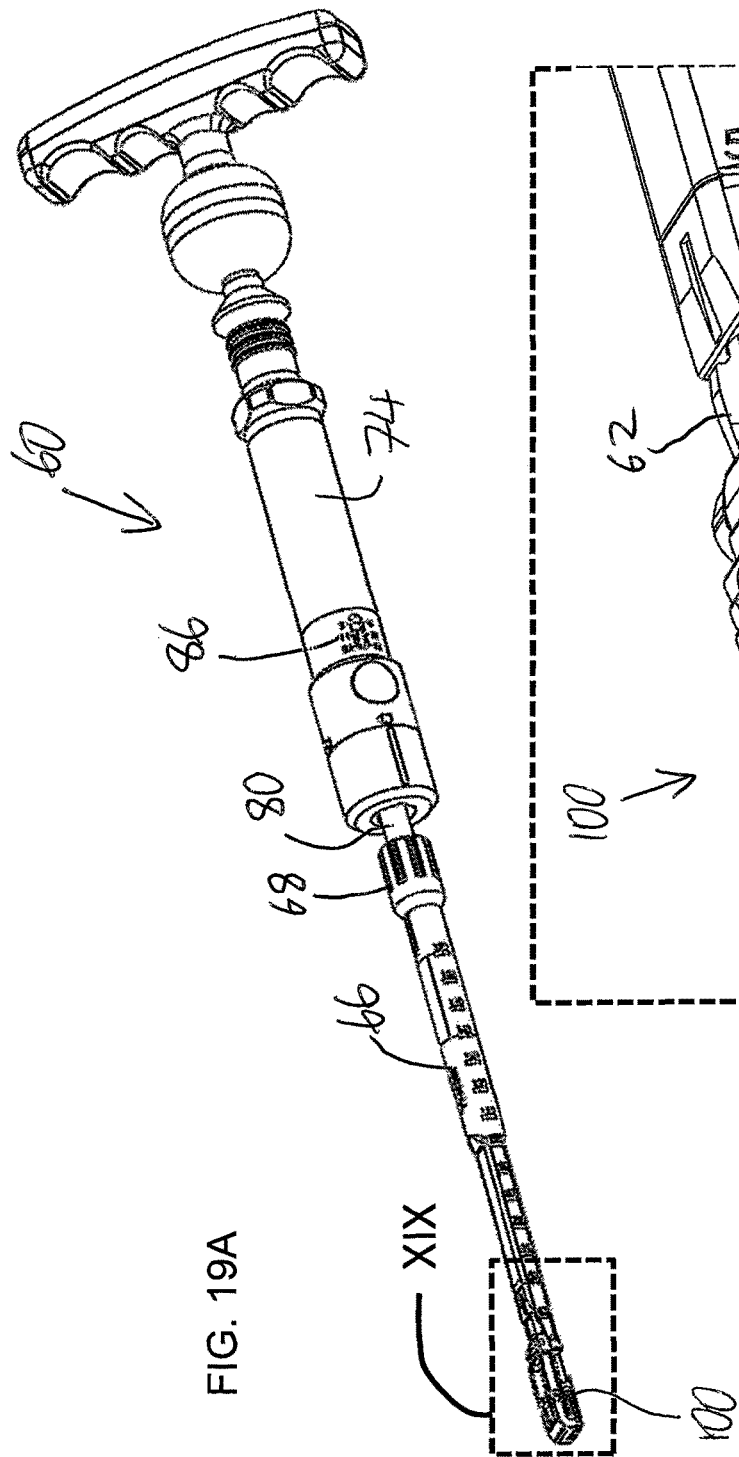
FIG. 19A is an isometric view illustrating the implant of FIG. 14A attached to a delivery system.
Figure 19B:
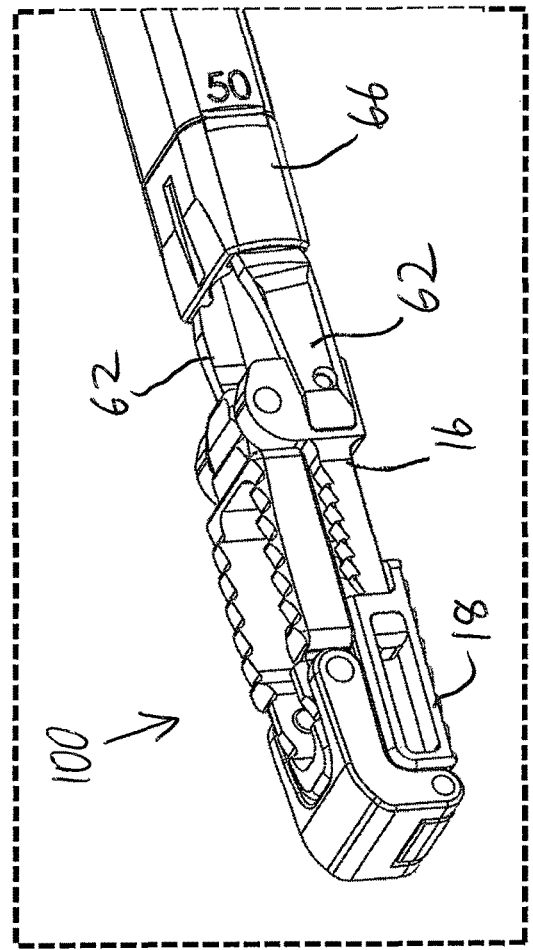
FIG. 19B is an enlarged view of the region of FIG. 19A designated XIX.
Figure 24A:
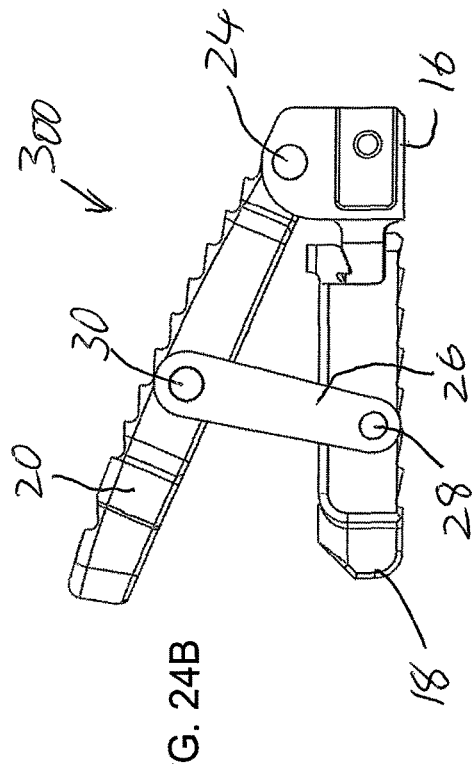
FIGS. 24A and 24B are side views of an implant according to a variant implementation of the implant of FIG. 14A illustrating a first alternative deployment of a linking segment, the implant being shown in a minimum angle and maximum angle state, respectively.
Figure 25A:
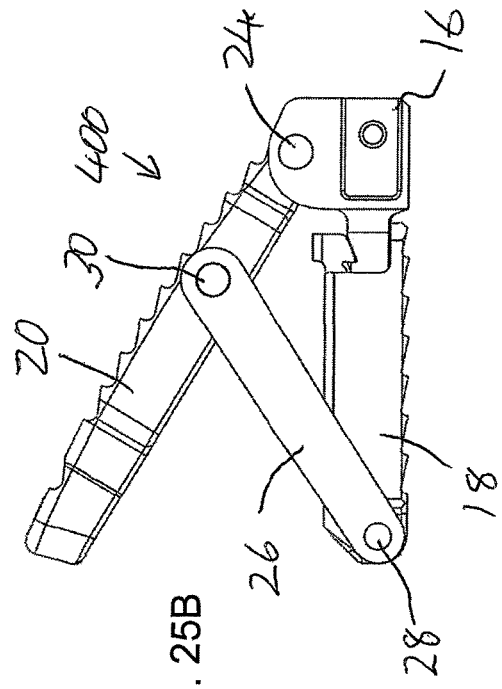
FIGS. 25A and 25B are side views of an implant according to a further variant implementation of the implant of FIG. 14A illustrating a further alternative deployment of a linking segment, the implant being shown in a minimum angle and maximum angle state, respectively.
Figure 24B:
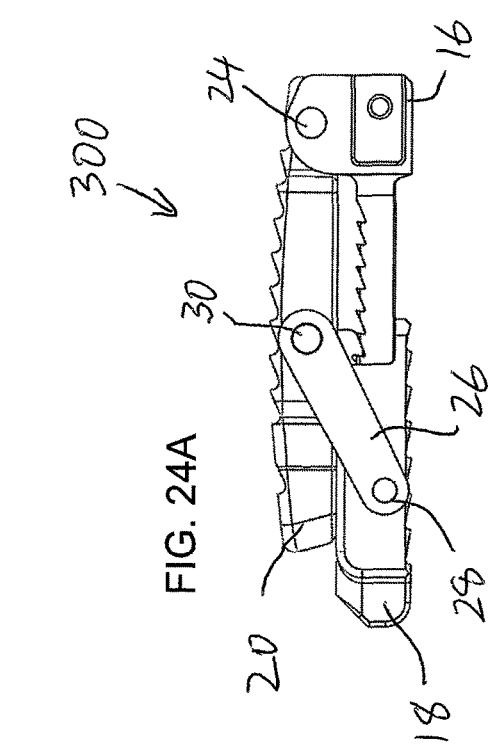
Figure 25B:
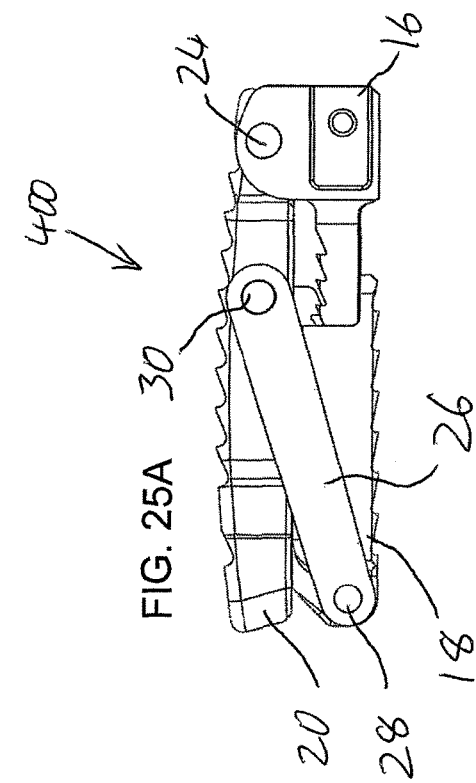

Engagement of a tip of deployment rod 32 with distal portion 18 may be by any suitable arrangement, such as via threaded engagement 36, as illustrated in FIG. 18A, or by a pin 38 and keyhole-slot 40 arrangement, as illustrated in FIGS. 21A-21C. Application of actuating force is preferably achieved by use of an actuator mechanism built into a handle of a delivery system, such as that of FIGS. 19A-20C, which allows continuous and controllable adjustment of the relative displacement of first and second portions 16, 18. After completion of the actuation, deployment rod 32 is preferably disengaged from second portion 18 and the deployment system is removed. The removable actuator structure is of particular value in interbody fusion applications, where the remaining inner volume of the implant is preferably contiguous with the aforementioned openings in the tissue contact surfaces to provide a through-channel for formation of a bone bridge between the vertebral endplates. Proximal opening 34 also allows for introduction and/or topping up of a filler material, such as natural or processed bone chips, medicaments and/or other fillers.

A non-limiting example of a delivery system, generally designated 60, is illustrated in FIGS. 19A-20C. The delivery system preferably includes a forked gripping mechanism including a pair of jaws 62 with complementary engagement features configured to engage lateral gripping regions 64 of the implant (visible in FIG. 14A). Jaws 62 are tightened against and released from engagement with implant 200 be advancing or retracting an outer sleeve 66 by rotation of a threaded collar 68.

Adjustment of the angle of contact surfaces of the implant is achieved by relative motion of jaws 62 pushing distally on first portion 16 while a counterforce is applied to second portion 18 via deployment rod 32. An exemplary mechanism for generating these forces is illustrated in FIGS. 20A and 20C.

In the example shown here, rotation of a handle 70 causes rotation of an insert 72 which is locked against axial motion relative to an outer housing 74, but is free to rotate. Insert 72 terminates at an internally threaded collar 76 which is engaged with a displacer element 78 which is mechanically restricted to axial motion within housing 74. Displacer element 78 engages an actuator sleeve 80 which is mechanically linked to outer sleeve 66 and jaws 62. Deployment rod 32 passes through the center of this entire assembly, and is fixed against axial displacement relative to housing 74 by a clamping element 82 which engages with a peripheral recess 84 in rod 32. As a result of this structure, rotation of handle 70 is effective to advance displacer element 78 relative to deployment rod 32, thereby applying the required forces via actuator sleeve 80 and jaws 62 to push proximal portion 16 towards distal portion 18 which is held by deployment rod 32. Preferably, an angle indicator 86 is associated with displacer element 78 so as to move relative to angle markings provided on housing 74, thereby indicating to a medical practitioner the angle currently reached by the contact surfaces of the implant.

Use of a removable actuation system typically requires provision of a separate locking mechanism. A wide range of locking mechanisms may be used to implement the present invention, including but not limited to, insertion of various propping elements, pins or bolts to fix the relative positions of two or more element of the implant. One particularly preferred subset of implementations of the present invention employs a ratchet configuration to maintain a desired deployed state of the device.

Specifically, first portion 16 and second portion 18 are preferably formed with complementary features defining a ratchet configuration. The complementary features as illustrated here include a series of ratchet teeth 42 associated with proximal portion 16 and a resiliently biased detent 44 associate with distal portion 18. The ratchet configuration is deployed to allow shortening of base 12 from its initial length through a range of lengths, and to oppose lengthening of the base.

Use of a ratchet configuration is particularly advantageous in that it allows unrestricted adjustment of the implant angle during deployment, while ensuring that the deployed angle is maintained very close to the maximum angle after the deployment system is released. The spacing of the ratchet teeth defines the distance between locking positions, defining at least one, and preferably at least three, and more preferably at least six, sequential states in which the implant locks. In some cases, ten or more teeth may be used to achieve a quasi-continuous range of locking positions.

Figure 3A:
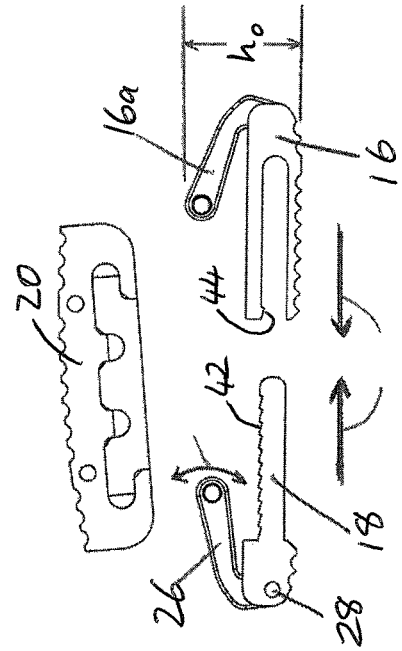
FIGS. 3A and 3B are an isometric and a side exploded view, respectively, showing the components of the implant of FIG. 1A.
Figure 3B:
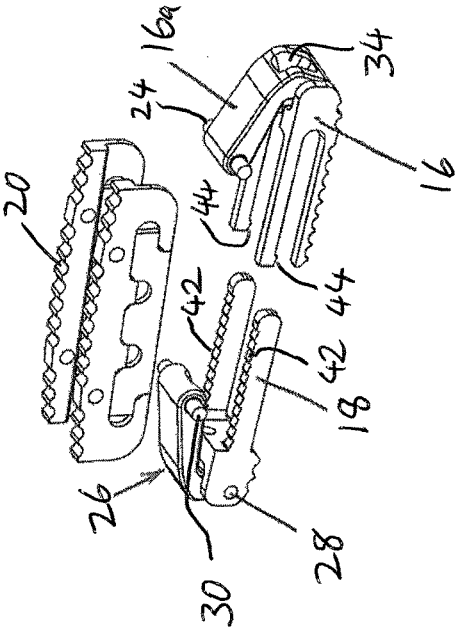

As mentioned above, it is typically preferable for the contact surfaces to have large openings, preferably including a major central opening running along at least part of a length of contact surface 14, which in some cases precludes central positioning of a ratchet configuration. Instead, particularly preferred implementations as illustrated herein employ a pair of ratchet arrangements deployed bilaterally, with a row of ratchet teeth 42 running along each side of a forked second portion 18, and a corresponding pair of spaced-apart biased detents 44 on first portion 16, as best seen in FIGS. 3A and 16A. This provides enhanced stability and rigidity to the deployed implant.

It should be noted that the ratchet configuration may be implemented in any orientation, and may arbitrarily be reversed between the proximal and distal portions. Thus, the series of ratchet teeth may be implemented as part of proximal portion 16, and may face "upwards" towards hinged element 20, "downwards" towards contact surface 14, inwards towards the internal space of the implant, or outwards.

As with all medical implants, it may in certain cases be desired to reposition or remove an implant, either during the deployment process or at a later date. Optionally, the rear surfaces of ratchet teeth 42 may have a relatively steep rise surface but may avoid full locking that would be achieved by an upright or undercut surface. This case would allow the locking to be overcome by application of sufficient outward force to overcome the reverse resistance of the ratchet configuration. More preferably, however, the present invention provides a ratchet release mechanism which facilitates reversal of the angular deployment without requiring application of large forces, as will now be described.

Ratchet Release Mechanism

By way of introduction, although described herein in the context of an adjustable angle implant, the ratchet and ratchet release mechanism described herein are applicable broadly to any adjustable implant in which adjustment is achieved by relative motion between two components which should normally be maintained at the displaced positions they reach at the end of the adjustment, but which must on occasion be released in order to readjust, reposition or remove the implant. Additional examples of implants in which such a mechanism may be used to advantage include, but are not limited to, adjustable dimension implants, such as expanding cages, with or without lordotic correction.

One particularly preferred but non-limiting example of a ratchet release mechanism is illustrated in FIGS. 16A and 16B. In order to facilitate release of the ratchet arrangement, and particularly in this case, simultaneous release of the bilateral pair of ratchet configurations, a crossbar 46 is mechanically linked to detents 44 so that upward displacement of crossbar 46 (in the orientation illustrated here) is effective to flex the resilient support structure and raise detents 44 out of engagement with ratchet teeth 42.

Disengagement of the ratchet configuration can thus be achieved by insertion of a suitably formed ratchet release element via proximal opening 34 so as to bear against crossbar 46 and release engagement of detents 44 with ratchet teeth 42, thereby allowing lengthening of base 12. In a particularly preferred set of implementations, in order to facilitate reversal of deployment when needed during the deployment process, this "ratchet release element" is integrated as part of deployment rod 32.

According to this approach, an engagement of deployment rod 32 with the distal portion of base 12, in this case, second portion 18, is configured to allow a first motion of the deployment rod while maintaining engagement of deployment rod 32 with the distal portion. Deployment rod 32 is provided with at least one feature deployed such that this first motion is effective to bring the at least one feature to bear on crossbar 46, thereby releasing engagement of detent(s) 44 with the ratchet teeth 42 to allow lengthening of the base.

A first implementation of these features is further illustrated in FIGS. 17A-18B. Specifically, the threaded engagement 36 between deployment rod 32 and second portion 18 allows a range of axial positions, depending upon the number of axial rotations of deployment rod 32 used to engage the threaded engagement. Deployment rod 32 her features an outward step 48 which is positioned such that, in a first axial position (FIG. 18A), when fully engaged with the threaded engagement 36, outward step 48 bears against crossbar 46, flexing it "upwards" as shown, thereby disengaging detents 44 from ratchet teeth 42 as shown in FIG. 17A. In a second axial position (FIG. 18B), when deployment rod 32 is engaged along only part of threaded engagement 36, outward step 48 is sufficiently withdrawn along the axis of the rod that crossbar 46 has returned to its unstressed state, and detents 44 are engaged with ratchet teeth 42 (FIG. 17B) to maintain the deployed state of the implant.

An alternative implementation is illustrated in FIGS. 21A-23C in which engagement between deployment rod 32 and distal (second) portion 18 is achieved through lateral pin 38 engaging a bayonet slot with a keyhole opening 40. As best seen in FIGS. 23A-23C, deployment rod 32 here assumes a first position with pin 38 upwards (FIG. 23A) in which the rod can be freely inserted and removed via keyhole opening 40, a first rotated position (FIG. 23B), rotated anticlockwise 90 degrees, in which pin 38 is already locked within the bayonet slot, and a second rotated position (FIG. 23C), rotated 180 degrees anticlockwise. As best seen in FIG. 21C, a region of deployment rod 32 positioned to come into alignment with crossbar 46 is provided with an eccentric cam surface 50, shown in this example with its maximum radius roughly opposite pin 38. As a result of this structure, rotation of deployment rod 32 from its first rotated position to its second rotated position is effective to bring cam surface 50 to bear on crossbar 46, thereby lifting detents 44 out of engagement with ratchet teeth 42.

Optionally, normal insertion of the implants of the present invention may be performed with the ratchet arrangement engaged, thereby achieving immediate, step-wise retention and stabilization of the implant during the adjustment process. In this case, the ratchet arrangement may provide audible and/or tactile feedback during the adjustment process which may be helpful to the medical practitioner. Further motion of deployment rod in order to release the ratchet mechanism would then only be performed in the event that readjusting, repositioning or removal of the implant becomes necessary.

Alternatively, the ratchet-release state may be used as the default state during deployment. In all cases, reengagement of the ratchet preferably occurs as part of the disengagement process, and prior to complete disengagement of deployment rod 32 from the distal portion, thereby helping to ensure that any forces acting on the implant do not disturb the intended adjusted state of the implant.

EXEMPLARY APPLICATIONS OF THE INVENTION

Implants of the present invention may be employed in a wide range of applications in which it is desired to adjust the relative angular deployment of two regions of tissue. By way of non-limiting particularly preferred examples, the invention is illustrated herein primarily in the context of various intervertebral applications.

Specifically, as illustrated schematically in FIGS. 5A-5B, the implant 10 (or 52, 200, 300, 400 or 500) is introduced between two vertebral bodies 900, 902 such that first contact surface 14 contacts an endplate of a first of the vertebral bodies 900 and second contact surface 22 contacts an endplate of a second of the vertebral bodies 902. Relative motion of first and second portions 16, 18 of base 12 is then used to actuate a change in angle between the contact surfaces, thereby changing an angle between the endplates.

The specific illustration of FIGS. 5A-5C is representative of a transforaminal or posterior approach, where the implant is used for lordotic correction to restore or increase an angle of lordosis between adjacent vertebral bodies, for example, as part of a transforaminal or posterior lumbar interbody fusion (TLIF or PLIF) procedure. FIG. 5A illustrates introduction of the implant. The placement of the deployed implant is illustrated in FIG. 5B, prior to adjustment, and in FIG. 5C after restoration of a lordotic angle.

FIGS. 6A and 6B illustrate schematically in plan view the deployment and final placement of implant 10 (or the other embodiments described herein) via a transforaminal approach.

FIG. 7 illustrates the final deployment via a posterior approach. In this case, bilateral use of a pair of implants is illustrated, where both implants contribute to the angular correction between the vertebral bodies. Use of more than one implant is encompassed within the scope of the invention also for transforaminal, lateral and other approaches.

Figure 10:
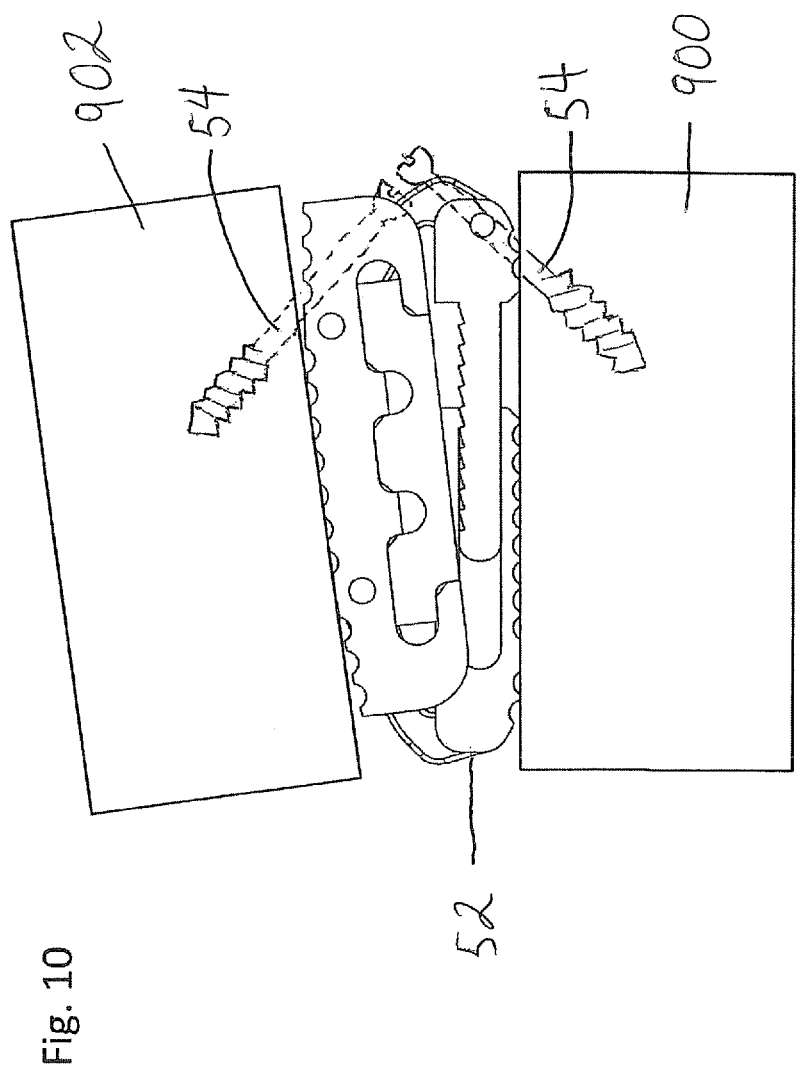
FIG. 10 is a schematic lateral view illustrating deployment of the implant of FIG. 8 deployed within an intervertebral space via an anterior approach.

It should be noted that the dimensions and proportions of the implant can readily be adapted according to the intended application and the available access route. For example, as illustrated in FIGS. 8 and 9, for anterior or lateral approach routes, it may be preferably to employ a single, anatomically shaped implant 52 sized to occupy a majority of the dimensions of the vertebral body endplates. For anterior placement, second portion 18 becomes the proximal end of base 12 relative to the anterior direction of approach, and the proximal opening 34 in this case traverses second portion 18 and/or connecting segment 26. Fixation of implant 52 may optionally be enhanced by insertion of anteriorly placed bone screws 54, as illustrated in FIG. 10.

Implant 52 may also be introduced via a lateral approach. For this purpose, gripping and actuation of the implant adjustment is typically performed via a laterally-engaged compression tool 56, as depicted schematically in FIGS. 11A and 11B.

As an alternative to lordotic correction, certain implementations of the present invention may be used to advantage to perform other types of angular adjustment or correction. By way of example, FIGS. 12A-13C illustrate the use of a suitably sized implementation of implant 10 to correct a scoliosis misalignment between adjacent vertebral bodies.

Figure 12A:
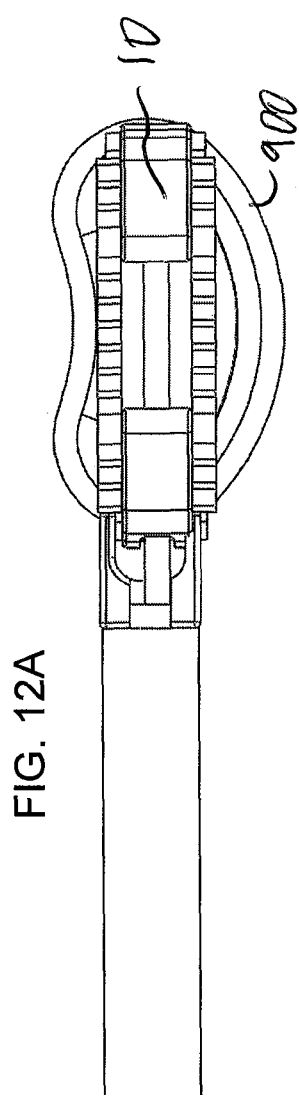
FIG. 12A is a schematic axial view illustrating introduction of the implant of FIG. 1A into an intervertebral space via a transverse approach.
Figure 12B:
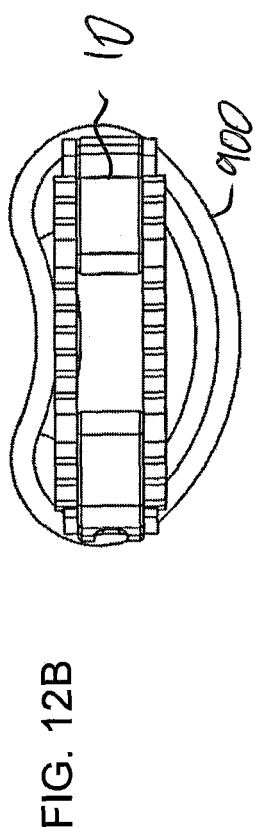
FIG. 12B is a view similar to FIG. 12A after deployment of the implant.

In the implementation of FIG. 12A-12B, a lateral approach is shown, thereby aligning the implant so that the angular correction occurs in a lateral direction. Clearly, and implant and delivery system similar to that illustrated in FIGS. 11A and 11B could be introduced via an anterior approach to achieve adjustment of lateral alignment deflection.

Figure 13C:
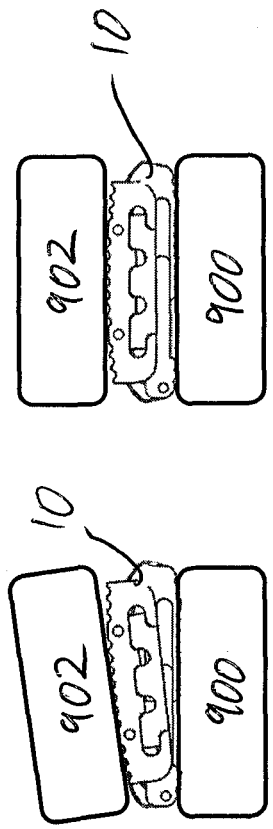
FIGS. 13A-13C are a sequence of schematic anterior views illustrating a process of correcting a scoliosis misalignment between adjacent vertebral bodies using the implant of FIG. 1A.
Figure 13B:
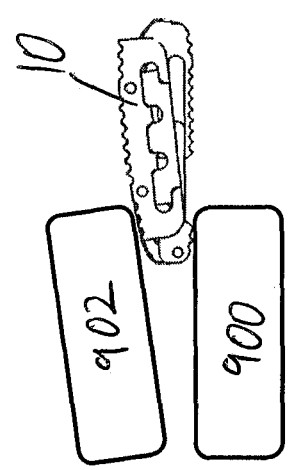
Figure 13A:
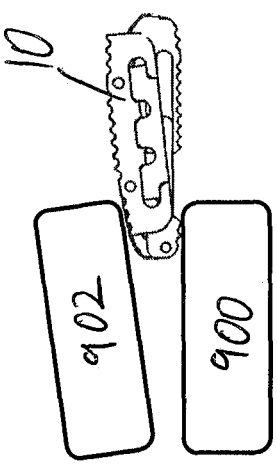
Figure 14A:
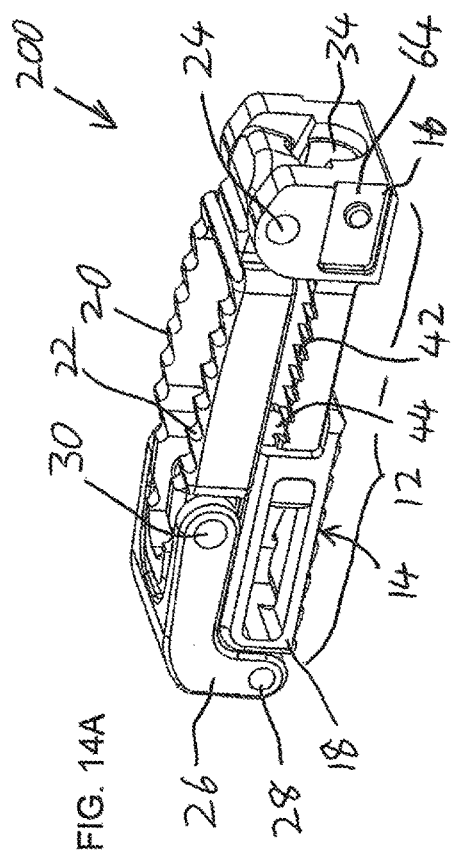
FIGS. 14A-14C are isometric views of an implant, constructed and operative according to an embodiment of the present invention, with an adjustable angle between two tissue contact surfaces, the implant being shown in a minimum-angle, an increased-angle and a maximum-angle state, respectively.
Figure 14C:
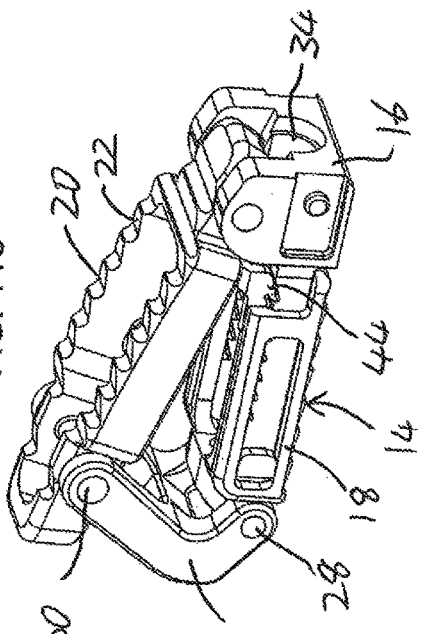
Figure 14B:
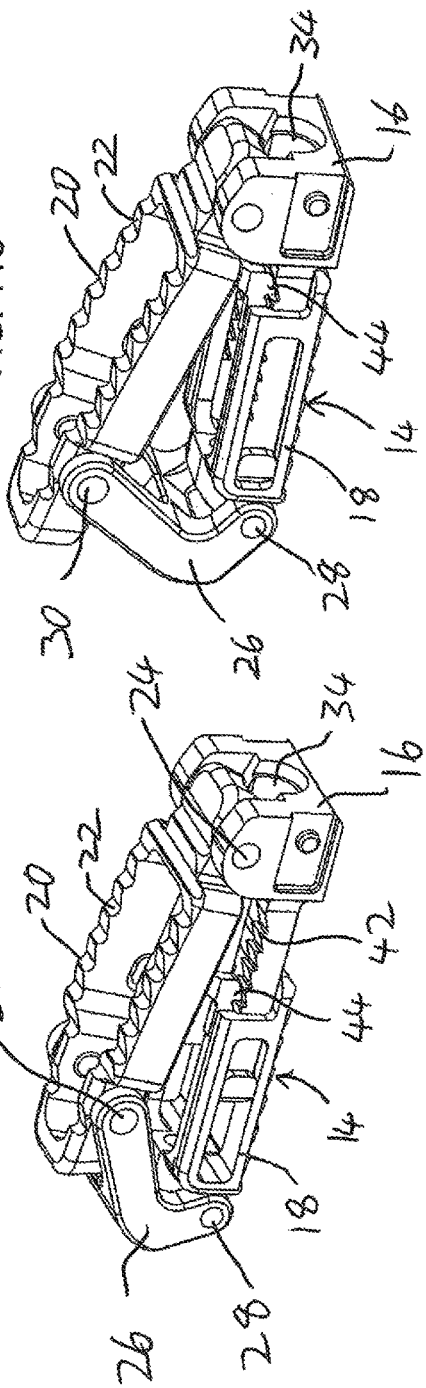

As illustrated in FIGS. 13A-13C, the endpoint of the adjustment in this case is typically roughly a zero angle inclination, so an implant implementation with a relatively small range of angular adjustment is typically sufficient. As with all applications, the actual adjustment state of the implant chosen by a medical practitioner in a clinical setting to achieve a desired alignment correction may vary considerably.

It will be appreciated that the above descriptions are intended only to serve as examples, and that many other embodiments are possible within the scope of the present invention as defined in the appended claims.

What is claimed is:

1. A system comprising an implant for insertion between two adjacent vertebral bodies, the implant comprising:
    (a) a base having a first contact surface for contacting a first of the adjacent vertebral bodies, said base comprising a first portion displaceable relative to a second portion, said base having an initial length and being shortened towards a second length through relative displacement of said first portion and said second portion;
    (b) a hinged element having a second contact surface for contacting a second of the adjacent vertebral bodies, said hinged element being interconnected with said first portion of said base at a hinge; and
    (c) a linking segment hingedly connected to said second portion of said base so as to be pivotable about a first axis and further hingedly connected to said hinged element so as to be pivotable about a second axis,
    wherein said base, said hinged element and said linking segment rigidly interconnect said hinged connections of said first axis, said second axis and said hinge in a rigid triangular geometry for any given length of said base such that shortening of said base from said initial length towards said second length causes said linking segment to push a region of said hinged element away from said base, thereby changing an angle of said second contact surface relative to said first contact surface,
    wherein each of said first and second contact surfaces spans a dimension of the implant parallel to said first axis and is provided with a plurality of projecting features configured for gripping respective endplates of the two adjacent vertebral bodies such that, when the implant is deployed between the first and second vertebral bodies and said base is shortened, said changing of said angle of said second contact surface relative to said first contact surface adjusts an extent of correction of a relative angle between the first and second vertebral bodies,
    wherein said second contact surface has a largest dimension referred to as a contact surface length, and wherein said linking segment has a dimension between said first axis and said second axis referred to as a linking segment length, said contact surface length being at least 40% longer than said linking segment length, and wherein said contact surface length is a majority of a total length of said implant when said base has said initial length.

2. The system of claim 1, wherein said hinged element has an end corresponding to a point on said hinged element furthest from said hinge, and wherein a location of hinged connection between said linking segment and said hinged element is distanced from said end by at least 10% of said contact surface length.

3. The system of claim 1, further comprising a deployment rod inserted via an opening in a proximal end of the implant and engaging a distal one of said first and second portions of said base such that a force applied to said proximal end of the implant in a distal direction can be opposed by a counterforce applied to said deployment rod, thereby causing shortening of said base.

4. The system of claim 1, wherein said first portion and said second portion are formed with complementary features defining a ratchet configuration comprising a series of ratchet teeth and a resiliently biased detent, said ratchet configuration being deployed to allow shortening of said base from said initial length through a range of lengths, and to oppose lengthening of said base.

5. The system of claim 4, further comprising a ratchet release element insertable via an opening in the implant and deployable to release engagement of said detent with said ratchet teeth to allow lengthening of said base.

6. The system of claim 4, further comprising a deployment rod inserted via an opening in a proximal end of the implant and engaging a distal one of said first and second portions of said base such that a force applied to said proximal end of the implant in a distal direction can be opposed by tension applied to said deployment rod, thereby causing shortening of said base.

7. The system of claim 6, wherein an engagement of said deployment rod with said distal portion is configured to allow a first motion of said deployment rod while maintaining engagement with said distal portion, and wherein said deployment rod has at least one feature deployed such that said first motion is effective to bring said at least one feature to bear on a part of said ratchet configuration so as to release engagement of said detent with said ratchet teeth to allow lengthening of said base.

8. The system of claim 7, wherein said engagement of said deployment rod with said distal portion is a threaded engagement, and wherein said first motion is a rotation effective to advance said deployment rod in relation to said threaded engagement.

9. The system of claim 1, wherein said first contact surface and said second contact surface are each partial surfaces having one or more openings totaling at least a quarter of a total area of a contact surface footprint.

10. The system of claim 1, wherein said first contact surface defines a first contact plane and said second contact surface defines a second contact plane, and wherein shortening of said base from said initial length towards said second length displaces said second contact plane through an angular range of at least 10° relative to said first contact plane.

11. A method comprising the steps of:
(a) introducing the implant of claim 1 between two vertebral bodies such that said first contact surface contacts an endplate of a first of said vertebral bodies and said second contact surface contacts an endplate of a second of said vertebral bodies; and
(b) causing relative motion of said first and second portions of said base so as to change an angle between said first and second contact surfaces, thereby changing an angle between said endplates.

12. The method of claim 11, wherein said introducing and said causing relative motion are performed so as to correct a scoliosis misalignment between adjacent vertebral bodies.

13. The method of claim 11, wherein said introducing and said causing relative motion are performed so as to restore or increase an angle of lordosis between adjacent vertebral bodies.

14. A method comprising the steps of:
(a) introducing two implants, each according to claim 1, between two vertebral bodies such that said first contact surface of each of said implants contacts an endplate of a first of said vertebral bodies and said second contact surface of each of said implants contacts an endplate of a second of said vertebral bodies; and
(b) for each of said implants, causing relative motion of said first and second portions of said base so as to change an angle between said first and second contact surfaces, thereby changing an angle between said endplates.

15. A system comprising an implant for insertion between two adjacent vertebral bodies, the implant comprising:
(a) a base having a first contact surface for contacting a first of the adjacent vertebral bodies, said base comprising a first portion displaceable relative to a second portion, said base having an initial length and being shortened towards a second length through relative displacement of said first portion and said second portion;
(b) a hinged element having a second contact surface for contacting a second of the adjacent vertebral bodies, said hinged element being interconnected with said first portion of said base at a hinge; and
(c) a linking segment hingedly connected to said second portion of said base so as to be pivotable about a first axis and further hingedly connected to said hinged element so as to be pivotable about a second axis,
wherein said base, said hinged element and said linking segment rigidly interconnect said hinged connections of said first axis, said second axis and said hinge in a rigid triangular geometry for any given length of said base such that shortening of said base from said initial length towards said second length causes said linking segment to push a region of said hinged element away from said base, thereby changing an angle of said second contact surface relative to said first contact surface,
wherein each of said first and second contact surfaces is provided with a plurality of projecting features configured for gripping respective endplates of the two adjacent vertebral bodies,
wherein said second contact surface has a largest dimension referred to as a contact surface length, and wherein said hinged element has an end corresponding to a point on said hinged element furthest from said hinge, a location of hinged connection between said linking segment and said hinged element being distanced from an end of said hinged element by at least 10% of said contact surface length.

16. The system of claim 15, wherein said linking segment has a dimension between said first axis and said second axis referred to as a linking segment length, said contact surface length being at least 40% longer than said linking segment length.

17. The system of claim 15, further comprising a deployment rod inserted via an opening in a proximal end of the implant and engaging a distal one of said first and second portions of said base such that a force applied to said proximal end of the implant in a distal direction can be opposed by a counterforce applied to said deployment rod, thereby causing shortening of said base.

18. The system of claim 15, wherein said first portion and said second portion are formed with complementary features defining a ratchet configuration comprising a series of ratchet teeth and a resiliently biased detent, said ratchet configuration being deployed to allow shortening of said base from said initial length through a range of lengths, and to oppose lengthening of said base.

19. The system of claim 18, further comprising a ratchet release element insertable via an opening in the implant and deployable to release engagement of said detent with said ratchet teeth to allow lengthening of said base.

20. The system of claim 18, further comprising a deployment rod inserted via an opening in a proximal end of the implant and engaging a distal one of said first and second portions of said base such that a force applied to said proximal end of the implant in a distal direction can be opposed by tension applied to said deployment rod, thereby causing shortening of said base.

21. The system of claim 20, wherein an engagement of said deployment rod with said distal portion is configured to allow a first motion of said deployment rod while maintaining engagement with said distal portion, and wherein said deployment rod has at least one feature deployed such that said first motion is effective to bring said at least one feature to bear on a part of said ratchet configuration so as to release engagement of said detent with said ratchet teeth to allow lengthening of said base.

22. The system of claim 21, wherein said engagement of said deployment rod with said distal portion is a threaded engagement, and wherein said first motion is a rotation effective to advance said deployment rod in relation to said threaded engagement.

23. The system of claim 15, wherein said first contact surface and said second contact surface are each partial surfaces having one or more openings totaling at least half of a total area of a contact surface footprint.

24. The system of claim 15, wherein said first contact surface defines a first contact plane and said second contact surface defines a second contact plane, and wherein shortening of said base from said initial length towards said second length displaces said second contact plane through an angular range of at least 10° relative to said first contact plane.

25. A method comprising the steps of:
(a) introducing the implant of claim 15 between two vertebral bodies such that said first contact surface contacts an endplate of a first of said vertebral bodies and said second contact surface contacts an endplate of a second of said vertebral bodies; and
(b) causing relative motion of said first and second portions of said base so as to change an angle between said first and second contact surfaces, thereby changing an angle between said endplates.

26. The method of claim 25, wherein said introducing and said causing relative motion are performed so as to correct a scoliosis misalignment between adjacent vertebral bodies.

27. The method of claim 25, wherein said introducing and said causing relative motion are performed so as to restore or increase an angle of lordosis between adjacent vertebral bodies.

28. A method comprising the steps of:
(a) introducing two implants, each according to claim 15, between two vertebral bodies such that said first contact surface of each of said implants contacts an endplate of a first of said vertebral bodies and said second contact surface of each of said implants contacts an endplate of a second of said vertebral bodies; and
(b) for each of said implants, causing relative motion of said first and second portions of said base so as to change an angle between said first and second contact surfaces, thereby changing an angle between said endplates.

* * * * *